United States Patent
De Kort et al.

(10) Patent No.: US 9,695,114 B2
(45) Date of Patent: Jul. 4, 2017

(54) PROCESSES FOR THE DIAZOTIZATION OF 2,5-DICHLOROANILINES

(71) Applicant: Monsanto Technology LLC, St. Louis, MO (US)

(72) Inventors: Bruno De Kort, St. Louis, MO (US); Matthew D. McReynolds, St. Louis, MO (US); John J. Parlow, St. Louis, MO (US); Rhonda S. Woerndle, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/106,072

(22) PCT Filed: Dec. 17, 2014

(86) PCT No.: PCT/US2014/070764
§ 371 (c)(1),
(2) Date: Jun. 17, 2016

(87) PCT Pub. No.: WO2015/095284
PCT Pub. Date: Jun. 25, 2015

(65) Prior Publication Data
US 2016/0318853 A1    Nov. 3, 2016

Related U.S. Application Data

(60) Provisional application No. 61/917,605, filed on Dec. 18, 2013.

(51) Int. Cl.
*C07C 245/20*  (2006.01)
*A01N 37/40*   (2006.01)
*C07C 37/045*  (2006.01)
*C07C 51/09*   (2006.01)
*C07C 209/36*  (2006.01)

(52) U.S. Cl.
CPC ............ *C07C 245/20* (2013.01); *A01N 37/40* (2013.01); *C07C 37/045* (2013.01); *C07C 51/09* (2013.01); *C07C 209/365* (2013.01)

(58) Field of Classification Search
CPC .................................................. C07C 245/20
See application file for complete search history.

(56) References Cited

U.S. PATENT DOCUMENTS

| | | |
|---|---|---|
| 3,013,054 A | 12/1961 | Richter |
| 3,345,157 A | 10/1967 | Richter |
| 4,005,151 A | 1/1977 | Wataya et al. |
| 4,161,611 A | 7/1979 | Kim |
| 4,326,882 A | 4/1982 | Richter et al. |
| 5,935,861 A | 8/1999 | Gnezda et al. |

FOREIGN PATENT DOCUMENTS

| | | |
|---|---|---|
| CN | 1830942 A | 9/2006 |
| CN | 1830943 A | 9/2006 |
| CN | 102942474 A | 2/2013 |
| CN | 102964221 A | 3/2013 |
| CN | 102125035 B | 7/2013 |
| EP | 2266975 A1 | 12/2010 |
| JP | 2008013472 | 1/2008 |
| PL | 133628 | 6/1986 |
| WO | 2006032518 A1 | 3/2006 |
| WO | 2006063999 A1 | 6/2006 |
| WO | 2007107298 A1 | 9/2007 |
| WO | 2008011539 A2 | 1/2008 |

OTHER PUBLICATIONS

Nemati, F., et al., "Green and Efficient Diazotization-Iodination of Arly Amines Using Cellulose Sulfuric Acid as a Biodegradable and Recyclable Proton Source Under Solvent-Free Condition," 2012, Scientia Iranica C, 19/6:1594-1596.
Obushak, N.D., et al., "Arenediazonium Tetrachlorocuprates(II). Modified Versions of the Meerwein and Sandmeyer Reactions," 2002, Russian J of Org Chem, 38/1:38-46, Abstract Only.
Patel, N.B., et al., "In vitro Antimicrobial and Antitubercular Studies of Novel 6-Substituted (Pyrrolidin-1-yl)-2(1H)-Pyridinones," 2012, Med Chem Res, 21:4108-4119.
Zhang, X., et al., "The Synthesis of Herbicides Dicamba," 2002, Pesticides, 41/11:13-14, 4 pages. (English Abstract Only).
Zhang, Y., et al., "The Study on the Preparation of Dicamba," 2002, Pesticides, 41/7:15-17, 2 pages. (English Abstract Only).
Zhang Y., et al., "Study on the O-Alkylation for 3,6-dichlorosalicylic Acid by Chloromethane," Huangong Shikan 2002, 16 (12) 45-48, 2 pages, (English Abstract Only).
Zollinger, H., "Chapter 13. Diazotization of Amines and Dediazoniation of Diazonium Ions," 1996, Supp F2: Chem of Amino, Nitroso, Nitro and Related Groups, Editor Saul Patai, John Wiley & Sons, Ltd., 37 pages.
Eckstein, Z., et al., "Comparison of Methods for Preparation of 3,6-dichloro-2-methoxy (Dicamba)," 1979, Przemysl Chemiczny, 58/10:533-536, 5 pages. (English Abstract Only).
Zhixun, L., et al., "A Novel Synthesis Method of 2,5-dichlorophenol," 2010, Huagong Shengchan Yu Jishu (Chemical Production Technology), 17/2:16-17, 4 pages. (English Abstract Only).
Kornblum, N., et al., "The Chemistry of Diazo Compounds. II. Evidence for a Free Radical Chain Mechanism in the Reduction of Diazonium Salts by Hypophosphorous Acid," 1950, The Chemistry of Diazonium Compounds, 3013-3021, 9 pages.
Korzeniowski, S.H., et al., "Reduction of Aryldiazonium Compounds in Nonpolar Media," 1977, J Org Chem, 42/8:1469-1470 (2 pages).
Mohan, M., et al., "Synthesis and Characterization of 4-arylazo-3,5-disubstituted-1H=pyrazole-1-carbodithioic Acids," 1986, Acta Pharm Jugosl, 36:13-45, 9 pages.

*Primary Examiner* — Shawquia Jackson
(74) *Attorney, Agent, or Firm* — Senniger Powers LLP; Erin C. Robert

(57) ABSTRACT

The present disclosure relates, in general, to processes for converting 2,5-dichloroaniline compounds to the corresponding 2,5-dichlorobenzenediazonium compounds, and further relates to processes for the preparation of 2,5-dichlorophenol which is a key intermediate used in the manufacture of dicamba.

20 Claims, 3 Drawing Sheets

PROCESSES FOR THE DIAZOTIZATION OF 2,5-DICHLOROANILINES

CROSS-REFERENCE TO RELATED APPLICATION

This application is a 371 National Stage Application of International Application No. PCT/US2014/070764, filed Dec. 17, 2014, which claims priority to U.S. Provisional Application No. 61/917,605 filed Dec. 18, 2013, which are incorporated herein by reference in their entirety.

FIELD OF THE INVENTION

The present disclosure relates, in general, to processes for converting 2,5-dichloroaniline compounds to the corresponding 2,5-dichlorobenzenediazonium compounds, and further relates to processes for the preparation of 2,5-dichlorophenol which is a key intermediate used in the manufacture of dicamba.

BACKGROUND OF THE INVENTION 3,6-Dichloro-2-methoxybenzoic acid (also known by its common name dicamba) is a highly effective and commercially important herbicide that is useful for controlling a wide variety of unwanted vegetation, including agricultural weeds. Convenient and economical methods of preparing dicamba, therefore, are of significant commercial importance.

A number of synthetic routes for the preparation of dicamba have been reported in the literature. One such route generally involves the conversion of 2,5-dichloroaniline to dicamba as shown in Scheme 1 below:

Scheme 1

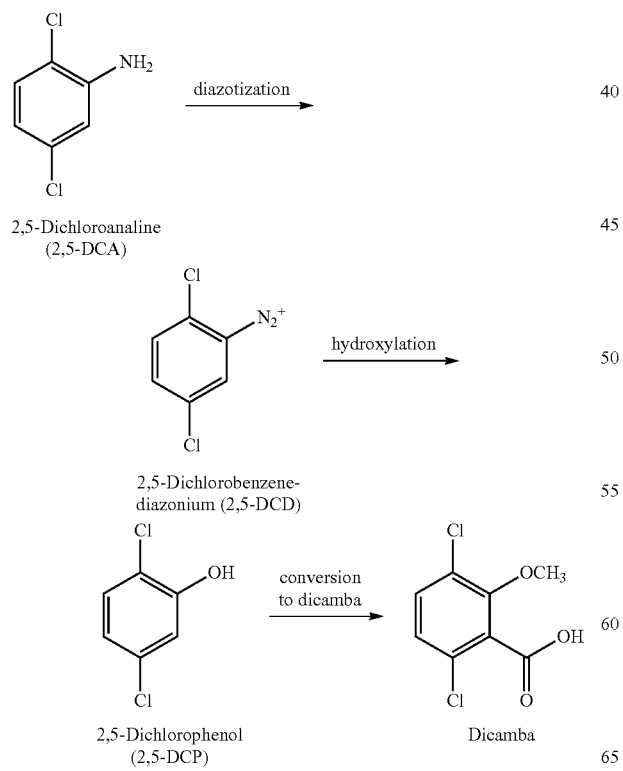

See, e.g., U.S. Pat. No. 4,161,611.

This route, however, typically requires certain process conditions (such as fine milling of the 2,5-dichloroanaline starting material, use of a large excess of sulfuric acid and/or concentrated sulfuric acid in the diazotizing step, etc.) in order to achieve an acceptable conversion of the 2,5-dichloroanaline to the 2,5-dichlorophenol on a commercial scale. The present disclosure provides improved processes that reduce or eliminate the need for such process conditions while still maintaining, or even improving, conversion of the 2,5-dichloroanaline to the 2,5-dichlorophenol.

BRIEF DESCRIPTION OF THE INVENTION

The present disclosure relates to processes for converting 2,5-dichloroaniline compounds to the corresponding 2,5-dichlorobenzenediazonium compounds.

In one aspect, the present disclosure relates to a process for the preparation of a compound corresponding in structure to Formula (IV):

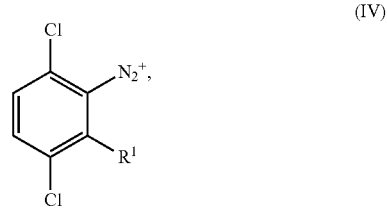

or a salt thereof, wherein $R^1$ is as defined in the present specification, and wherein the process comprises contacting a compound corresponding in structure to Formula (III):

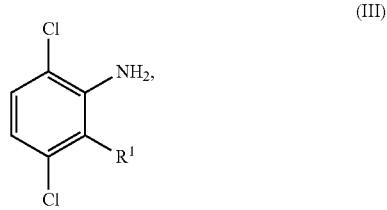

or a salt thereof, with a diazotizing agent in a reaction medium comprising sulfuric acid and an organic acid selected from the group consisting of $C_2$-$C_6$-alkanoic acids and halo-$C_1$-$C_6$-alkanoic acids to generate a diazonium product mixture comprising the compound or salt of Formula (IV).

In another aspect, the present disclosure relates to a process for the preparation of a compound corresponding in structure to Formula (IV):

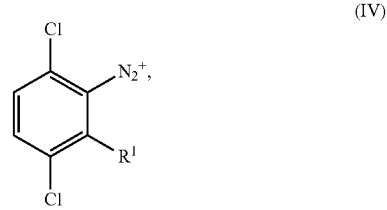

or a salt thereof, wherein $R^1$ is as defined in the present specification, and wherein the process comprises:

forming a reaction medium comprising sulfuric acid; an organic acid selected from the group consisting of $C_2$-$C_6$-alkanoic acids and halo-$C_1$-$C_6$-alkanoic acids; and, optionally, a first amount of a compound corresponding in structure to Formula (III):

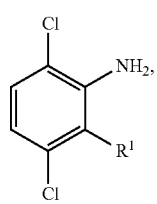

(III)

or a salt thereof; and introducing into the reaction medium a second amount of the compound or salt of the compound of Formula (III), and a diazotizing agent, to generate a diazonium product mixture comprising the compound or salt of Formula (IV).

In another aspect, the present disclosure relates to a process for the preparation of a compound corresponding in structure to Formula (IV):

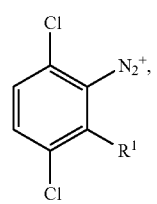

(IV)

or a salt thereof, wherein $R^1$ is as defined in the present specification, and wherein the process comprises:

forming a reaction medium comprising sulfuric acid; an organic acid selected from the group consisting of $C_2$-$C_6$-alkanoic acids and halo-$C_1$-$C_6$-alkanoic acids; and a compound corresponding in structure to Formula (III):

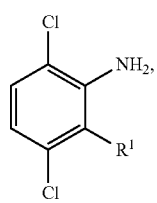

(III)

or a salt thereof; and introducing into the reaction medium a diazotizing agent to generate a diazonium product mixture comprising the compound or salt of Formula (IV).

In another aspect, the present disclosure relates to a process as stated above that further comprises hydrolyzing the compound or salt of Formula (IV) to a compound corresponding in structure to Formula (V):

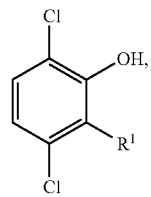

(V)

or a salt thereof, wherein $R^1$ is as defined in the present specification.

In another aspect, the present disclosure relates to a process for the preparation of a compound corresponding in structure to Formula (VI):

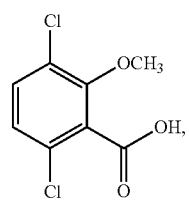

(VI)

or a salt thereof, wherein the process comprises:

contacting a compound corresponding in structure to Formula (III-a):

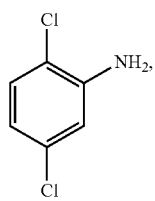

(III-a)

or a salt thereof, with a diazotizing agent in a reaction medium comprising sulfuric acid and an organic acid selected from the group consisting of $C_2$-$C_6$-alkanoic acids and halo-$C_1$-$C_6$-alkanoic acids to generate a diazonium product mixture comprising a compound corresponding in structure to Formula (IV-a):

(IV-a)

or a salt thereof;

hydrolyzing the compound or salt of Formula (IV-a) to generate a phenol product mixture comprising a compound corresponding in structure to Formula (V-a):

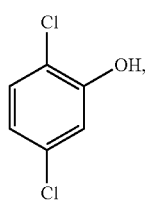

(V-a)

or a salt thereof; and carboxylating the compound or salt of Formula (V-a) to generate a carboxylated product mixture comprising a compound corresponding in structure to Formula (V-b):

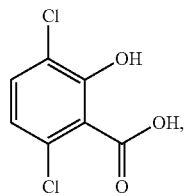

(V-b)

or a salt thereof; and converting the compound or salt of Formula (VI-b) to the compound or salt of Formula (VI).

DETAILED DESCRIPTION OF THE INVENTION

Figure 1:
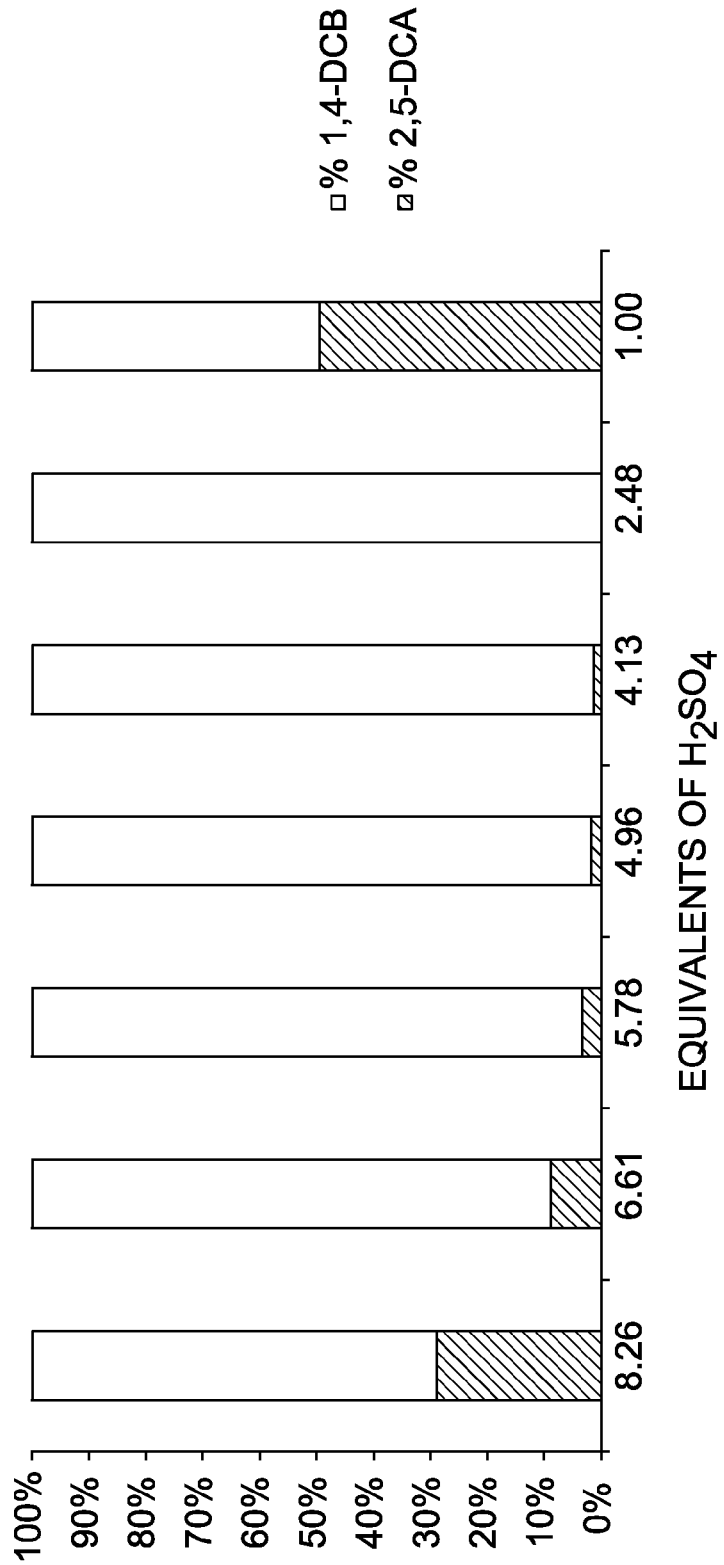
FIG. 1 is a bar chart illustrating the percent conversion (based on normalized peak absorbance at 208 nm by HPLC) of 2,5-dichloroaniline to 2,5-dichlorobenzenediazonium (quantified as 1,4-dichlorobenzene) as a function of equivalents of sulfuric acid relative to the 2,5-dichloroaniline.

This written description uses examples to disclose the invention, including the best mode, and also to enable any person skilled in the art to practice the invention, including making and using any of the disclosed salts, substances, or compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements.

I. Definitions

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "about" generally refers to a range of numbers that one of skill in the art would consider equivalent to the recited value (i.e., having the same function or result). In many instances, the term "about" may include numbers that are rounded to the nearest significant figure.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The term "sodium nitrite$_{(aq)}$" refers to an aqueous solution of sodium nitrite.

The term "sulfuric acid$_{(aq)}$" refers to an aqueous solution of sulfuric acid.

The abbreviation "AcOH" means acetic acid.

The abbreviation "2,5-DCA" means 2,5-dichloroaniline.

The abbreviation "1,4-DCB" means 1,4-dichlorobenzene.

The abbreviation "2,5-DCD" means 2,5-dichlorobenzenediazonium.

The abbreviation "1,4-DCNB" means 1,4-dichloronitrobenzene.

The abbreviation "2,5-DCP" means 2,5-dichlorophenol.

II. Diazotization Of 2,5-Dichloroanilines

The present disclosure relates, in part, to processes for diazotizing a 2,5-dichloroaniline compound to provide the corresponding 2,5-dichlorobenzenediazonium compound. In particular, the present disclosure relates to processes for diazotizing 2,5-dichloroaniline to provide 2,5-dichlorobenzenediazonium. The 2,5-dichlorobenzenediazonium prepared can be hydrolyzed to provide the corresponding 2,5-dichlorophenol, a key intermediate used in the manufacture of dicamba.

Among other process improvements, it has been discovered that 2,5-dichloroaniline and its sulfate salt have improved solubility in a reaction medium comprising sulfuric acid and an organic acid selected from the group consisting of $C_2$-$C_6$-alkanoic acids (such as acetic acid) and halo-$C_1$-$C_6$-alkanoic acids (such as trifluoroacetic acid) relative to a corresponding reaction medium lacking the organic acid. It has been further discovered that conducting the diazotization reaction in such a reaction medium results in a more efficient and homogeneous conversion of the 2,5-dichloroaniline to the corresponding 2,5-dichlorobenzenediazonium. Excellent conversions of the 2,5-dichloroaniline to the 2,5-dichlorobenzenediazonium have been achieved using an organic acid/sulfuric acid reaction medium.

Due to its cheaper cost relative to more expensive organic reagents, sodium nitrite ($NaNO_2$) frequently is selected as a diazotizing agent for diazotization reactions conducted in an industrial setting. When sodium nitrite is used as the diazotizing reagent, the reaction typically is conducted in an acid medium in order to generate nitrous acid which is then consumed in the diazotizing step. Sulfuric acid ($H_2SO_4$) frequently is used as the acid medium for such diazotization reactions. Scheme 2 below illustrates the hypothesized reaction pathway for the generation of nitrous acid from sodium nitrite in a sulfuric acid medium and the subsequent generation of nitrosylsulfuric acid. As discussed later, the nitrosylsulfuric acid generated reacts with the 2,5-dichloroaniline starting material to provide the 2,5-dichlorobenzenediazonium product.

Scheme 2

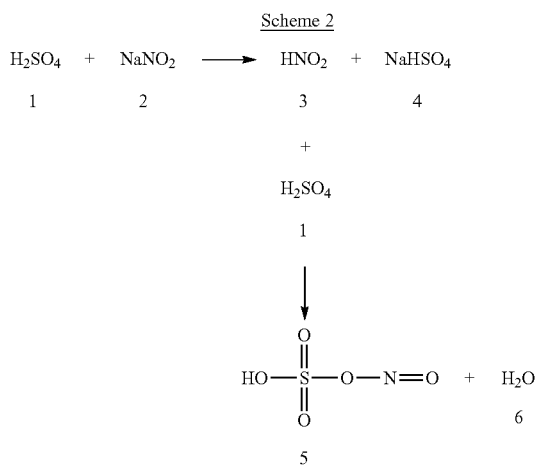

It is believed that sodium nitrite 2 reacts with an equivalent of sulfuric acid 1 to produce nitrous acid 3 and sodium bisulfate 4. Under strong acidic conditions, the nitrous acid 3 then reacts with sulfuric acid 1 to generate nitrosylsulfuric acid 5 and water 6.

When the diazotization reaction takes place in a sulfuric acid medium, the free 2,5-dichloroaniline (not the sulfate salt of 2,5-dichloroaniline) serves as the nucleophile and reacts with the nitrosylsulfuric acid which serves as the electrophile. The solubility of 2,5-dichloroaniline in concentrated and aqueous solutions of sulfuric acid is relatively low, and conversion of the 2,5-dichloroaniline to the corresponding 2,5-dichlorobenzenediazonium is limited by such solubility. Therefore, a large amount of the sulfuric acid (and/or higher concentrations of the sulfuric acid) generally is required to achieve an acceptable conversion and the process is not efficient for commercial-scale manufacturing.

One approach suggested in the literature for addressing this problem has been to mill the 2,5-dichloroaniline to a fine particle size in order to improve solubility. U.S. Pat. No. 4,005,151, for example, describes ball milling the 2,5-dichloroaniline starting material used in the diazotizing step.

Another approach suggested in the literature has been to use concentrated sulfuric acid, or at least higher concentrations of aqueous sulfuric acid, as the reaction medium. U.S. Pat. No. 4,326,882, for example, describes the use of concentrated sulfuric acid in the diazotizing step.

Use of an alternative mineral acid medium such as a hydrochloric acid (HCl) medium is not a satisfactory alternative. The solubility of 2,5-dichloroaniline in concentrated and aqueous solutions of hydrochloric acid, for example, also is relatively low and conversion of the 2,5-dichloroaniline to the corresponding 2,5-dichlorobenzenediazonium is similarly limited by solubility. In addition, use of hydrochloric acid as the acid medium allows the chloride (Cl$^-$) to compete as a nucleophile during the subsequent hydrolysis of the 2,5-dichlorodiazonium to the 2,5-dichlorophenol potentially resulting in a 3-chloro substituent instead of the desired 3-hydroxy substituent. Similarly, nitric acid and other mineral acids would present the same problem, e.g., use of nitric acid as the acid medium, to the extent even practical, would allow the nitrate (NO$_3^-$) to compete as a nucleophile during the subsequent hydrolysis of the 2,5-dichlorodiazonium to the 2,5-dichlorophenol potentially resulting in a 3-nitro substituent instead of the desired 3-hydroxy substituent. Accordingly, sulfuric acid is generally preferred over other mineral acids when the 2,5-dichlorobenzenediazonium generated is to be further hydrolyzed to the 2,5-dichlorophenol.

Use of the organic acid/sulfuric acid reaction medium of the present disclosure provides several advantages over a conventional sulfuric acid reaction medium including the following:

(1) Excellent conversions of the 2,5-dichloroaniline to the 2,5-dichlorobenzenediazonium are achieved.

(2) Additional processing of the 2,5-dichloroaniline starting material (e.g., fine milling such as ball milling) is not required to help solubilize the 2,5-dichloroaniline.

(3) Sulfuric acid handling requirements are reduced as a lower volume of sulfuric acid is needed for the diazotization reaction.

(4) Where the overall process also includes a hydroxylation step in which the 2,5-dichlorobenzenediazonium is converted to the 2,5-dichlorophenol, the organic acid helps to reduce plugging of the distillation apparatus during distillation.

(5) Where the overall process also includes a step in which 1,4-dichloronitrobenzene is reduced to 2,5-dichloroaniline, the organic acid can be used in the reducing step allowing for the direct transfer of the reaction mixture comprising the 2,5-chloroaniline into the diazotization reactor.

(6) Where the overall process also includes both a reducing step and a hydroxylation step as discussed above, the organic acid can be recovered from the hydroxylation step and recycled back to the reducing step.

Although primarily illustrated throughout this application with respect to 2,5-dichloroaniline, the improved process can be used to diazotize other 2,5-dichloroaniline compounds that are further substituted at the 3-position of the ring.

Accordingly, in one embodiment, the present disclosure relates to a process for the preparation of a compound corresponding in structure to Formula (IV):

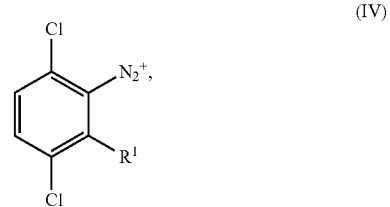

or a salt thereof, the process comprising contacting a compound corresponding in structure to Formula (III):

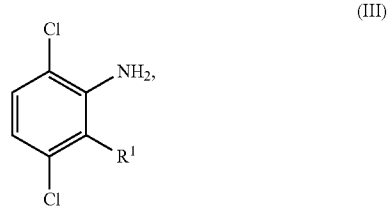

or a salt thereof, with a diazotizing agent in a reaction medium comprising sulfuric acid and an organic acid selected from the group consisting of $C_2$-$C_6$-alkanoic acids and halo-$C_1$-$C_6$-alkanoic acids to generate a diazonium product mixture comprising the compound or salt of Formula (IV);

wherein:

$R^1$ is selected from the group consisting of hydrogen, halogen, cyano, —$CH_3$, —$CH_2OH$, —$C(O)R^2$, —$C(O)OR^3$, and —$B(R^4)_2$;

$R^2$ is selected from the group consisting of hydrogen, $C_1$-$C_6$-alkyl, and —$NR^A R^B$; wherein $R^A$ and $R^B$ are independently selected from the group consisting of hydrogen and $C_1$-$C_6$-alkyl; and $R^3$ is selected from the group consisting of hydrogen and $C_1$-$C_6$-alkyl; and $R^4$ is selected from the group consisting of hydroxy and $C_1$-$C_6$-alkyl.

In one aspect, $R^1$ is hydrogen (i.e., the compound of Formula (III) is 2,5-dichloroanaline). In another aspect, $R^1$ is selected from the group consisting of halogen, cyano, —$CH_3$, —$CH_2OH$, —$C(O)R^2$, —$C(O)OR^3$, and —$B(R^4)_2$; and $R^2$, $R^3$, and $R^4$ are as defined above (i.e., the compound of Formula (III) is a 2,5-dichloroanaline compound that is further substituted at the 3-position of the ring).

In one embodiment, the present disclosure relates to a process for the preparation of a compound corresponding in structure Formula (IV):

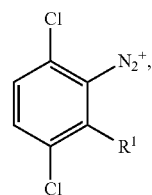

(IV)

or a salt thereof, the process comprising:

forming a reaction medium comprising sulfuric acid; an organic acid selected from the group consisting of $C_2$-$C_6$-alkanoic acids and halo-$C_1$-$C_6$-alkanoic acids; and, optionally, a first amount of a compound corresponding in structure to Formula (III):

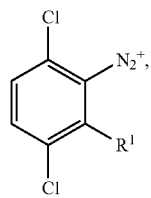

(III)

or a salt thereof; and introducing into the reaction medium a second amount of the compound or salt of the compound of Formula (III), and a diazotizing agent, to generate a diazonium product mixture comprising the compound or salt of Formula (IV);

wherein:

$R^1$ is selected from the group consisting of hydrogen, halogen, cyano, —$CH_3$, —$CH_2OH$, —$C(O)R^2$, —$C(O)OR^3$, and —$B(R^4)_2$;

$R^2$ is selected from the group consisting of hydrogen, $C_1$-$C_6$-alkyl, and —$NR^A R^B$; wherein $R^A$ and $R^B$ are independently selected from the group consisting of hydrogen and $C_1$-$C_6$-alkyl; and $R^3$ is selected from the group consisting of hydrogen and $C_1$-$C_6$-alkyl; and $R^4$ is selected from the group consisting of hydroxy and $C_1$-$C_6$-alkyl.

In one aspect, $R^1$ is hydrogen (i.e., the compound of Formula (III) is 2,5-dichloroanaline). In another aspect, $R^1$ is selected from the group consisting of halogen, cyano, —$CH_3$, —$CH_2OH$, —$C(O)R^2$, —$C(O)OR^3$, and —$B(R^4)_2$; and $R^2$, $R^3$, and $R^4$ are as defined above (i.e., the compound of Formula (III) is a 2,5-dichloroanaline compound that is further substituted at the 3-position of the ring).

In one embodiment, the present disclosure relates to a process for the preparation of a compound corresponding in structure to Formula (IV):

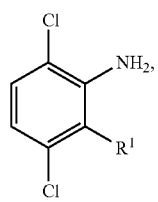

(IV)

or a salt thereof, the process comprising:

forming a reaction medium comprising sulfuric acid; an organic acid selected from the group consisting of $C_2$-$C_6$-alkanoic acids and halo-$C_1$-$C_6$-alkanoic acids; and a compound corresponding in structure to Formula (III):

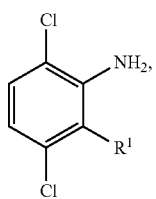

(III)

or a salt thereof; and introducing into the reaction medium a diazotizing agent to generate a diazonium product mixture comprising the compound or salt of Formula (IV);

wherein:

$R^1$ is selected from the group consisting of hydrogen, halogen, cyano, —$CH_3$, —$CH_2OH$, —$C(O)R^2$, —$C(O)OR^3$, and —$B(R^4)_2$;

$R^2$ is selected from the group consisting of hydrogen, $C_1$-$C_6$-alkyl, and —$NR^A R^B$; wherein $R^A$ and $R^B$ are independently selected from the group consisting of hydrogen and $C_1$-$C_6$-alkyl; and $R^3$ is selected from the group consisting of hydrogen and $C_1$-$C_6$-alkyl; and $R^4$ is selected from the group consisting of hydroxy and $C_1$-$C_6$-alkyl.

In one aspect, $R^1$ is hydrogen (i.e., the compound of Formula (III) is 2,5-dichloroanaline). In another aspect, $R^1$ is selected from the group consisting of halogen, cyano, —$CH_3$, —$CH_2OH$, —$C(O)R^2$, —$C(O)OR^3$, and —$B(R^4)_2$; and $R^2$, $R^3$, and $R^4$ are as defined above (i.e., the compound of Formula (III) is a 2,5-dichloroanaline compound that is further substituted at the 3-position of the ring).

Scheme 3 below provides an illustration of the overall reaction when the Compound of Formula (III) is 2,5-dichloroaniline and the organic acid is acetic acid:

Acetic acid 8 functions as a co-solvent to improve solubility of 2,5-dichloroaniline 7 and its sulfate salt 9 in the reaction medium enabling full conversion to 2,5-dichlorobenzenediazonium salt 10. Similarly, acetic acid 8 functions as a co-solvent to improve solubility of 2,5-dichlorobenzenedi-

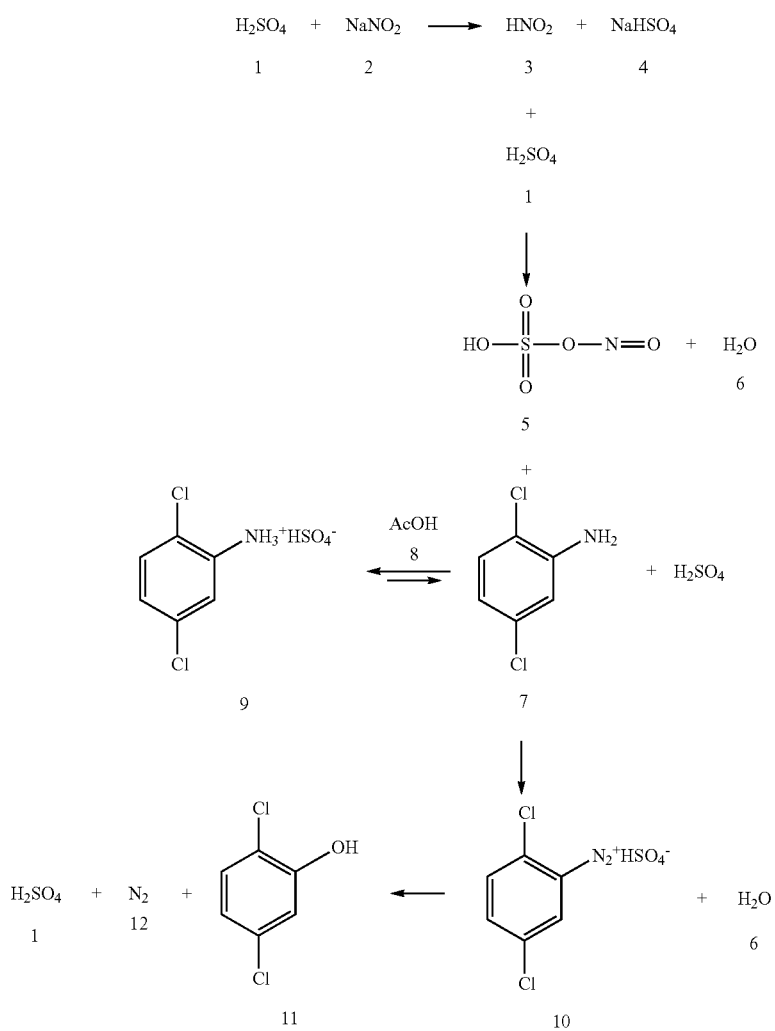

Scheme 3

In general, a reaction medium comprising sulfuric acid 1, 2,5-dichloroaniline 7, and acetic acid 8 is prepared. As needed, the reaction medium is cooled to a suitable temperature (e.g., from about 0° C. to about 25° C.). Under such conditions, the reaction medium typically will be a slurry comprising 2,5-dichloroaniline 7 and its sulfate salt 9.

Sodium nitrite 2 is added to the reaction medium (e.g., subsurface addition of an aqueous solution of sodium nitrite 2). The addition of sodium nitrite 2 to the reaction medium generates nitrosylsulfuric acid 5 which then reacts with 2,5-dichloroaniline 7 to provide 2,5-dichlorobenzenediazonium salt 10. The diazotization reaction proceeds quickly and substantially all of 2,5-dichloroaniline 7 reacts and is converted to 2,5-dichlorobenzenediazonium salt 10. As previously noted, 2,5-dichloroaniline 7 (not the sulfate salt of 2,5-dichloroaniline 9) serves as the nucleophile and reacts with nitrosylsulfuric acid 5 which serves as the electrophile.

azonium salt 10 in the reaction medium and effectively solubilizes that product as it is generated.

2,5-Dichlorobenzenediazonium 10 can be converted to 2,5-dichlorophenol 11 in a subsequent step as shown in Scheme 3. Water 6 can serve as a nucleophile, for example, and react with 2,5-dichlorobenzenediazonium salt 10 to provide 2,5-dichlorophenol 11, nitrogen gas 12, and sulfuric acid 1. Because diazonium salts frequently are unstable, 2,5-dichlorobenzenediazonium salt 10 generally is not isolated from the reaction medium prior to conversion to 2,5-dichlorophenol 11.

A. Diazotization Reaction Medium

The organic acid employed as a co-solvent with the sulfuric acid in the preparation of the reaction medium generally is one that does not react with sulfuric acid and that solubilizes the compound or salt of Formula (III). In one embodiment, the organic acid is selected from the group consisting of $C_2$-$C_6$-alkanoic acids and halo-$C_1$-$C_6$-alkanoic acids. In one aspect, the organic acid is a $C_2$-$C_6$-alkanoic acid. In another aspect, the organic acid is a halo-$C_1$-$C_6$-alkanoic acid. In another aspect, the organic acid is selected from the group consisting of acetic acid and trifluoroacetic acid. In another aspect, the organic acid is acetic acid. In another aspect, the organic acid is trifluoroacetic acid. In another aspect, the reaction medium further comprises water.

i. Initial Medium Comprises Compound of Formula (III)

In certain embodiments, the initial reaction medium comprises the entire amount, or substantially the entire amount, of the compound or salt of Formula (III) to be charged to the process. This reaction medium can be prepared in any suitable manner prior to the introduction of the diazotizing agent. In one embodiment, for example, the reaction medium is prepared by: (i) forming a first mixture comprising the organic acid and the compound or salt of Formula (III); and (ii) adding the sulfuric acid to the first mixture to form the reaction medium. In another embodiment, the reaction medium is prepared by: (i) forming a first mixture comprising the sulfuric acid and the compound or salt of Formula (III); and adding the organic acid to the first mixture to form the reaction medium. In another embodiment, the reaction medium is prepared by: (i) forming a first mixture comprising the sulfuric acid and the organic acid; and (ii) adding the first mixture to the compound or salt of Formula (III) to form the reaction medium. In one aspect, concentrated sulfuric acid (e.g., about 98 weight percent sulfuric acid) is used in the preparation of the reaction medium. In another aspect, an aqueous solution of sulfuric acid (e.g., about 75 weight percent sulfuric acid or greater) is used in the preparation of the reaction medium. In another aspect, glacial acetic acid is used in the preparation of the reaction medium. In another aspect, an aqueous solution of acetic acid (e.g., about 75 weight percent acetic acid or greater) is used in the preparation of the reaction medium.

The reaction medium generally will comprise from about 1 molar equivalent to about 33 molar equivalents of the organic acid per mole of the compound or salt of Formula (III). In one embodiment, the reaction medium comprises from about 5 molar equivalents to about 33 molar equivalents of the organic acid per mole of the compound or salt of Formula (III). In one aspect, the reaction medium comprises from about 6 molar equivalents to about 18 molar equivalents of the organic acid per mole of the compound or salt of Formula (III). In another aspect, the reaction medium comprises at least about 7 molar equivalents of the organic acid per mole of the compound or salt of Formula (III). In another aspect, the reaction medium comprises from about 7 molar equivalents to about 9 molar equivalents of the organic acid per mole of the compound or salt of Formula (III).

The reaction medium also generally comprises from about 1 molar equivalent to about 11 molar equivalents of the sulfuric acid per mole of the compound or salt of Formula (III). In one embodiment, the reaction medium comprises at least about 2 molar equivalents of the sulfuric acid per mole of the compound or salt of Formula (III). In one aspect, the reaction medium comprises from about 2 molar equivalents to about 8 molar equivalents of the sulfuric acid per mole of the compound or salt of Formula (III). In another aspect, the reaction medium comprises from about 2 molar equivalents to about 6 molar equivalents of the sulfuric acid per mole of the compound or salt of Formula (III). In another aspect, the reaction medium comprises from about 2 molar equivalents to about 4 molar equivalents of the sulfuric acid per mole of the compound or salt of Formula (III). In another aspect, the reaction medium comprises about 2.5 moles of the organic acid per mole of the sulfuric acid.

In one embodiment, the molar ratio of the organic acid to the sulfuric acid in the reaction medium is from about 30:1 to about 1:10. In one aspect, the molar ratio of the organic acid to the sulfuric acid is from about 10:1 to about 1:2. In another aspect, the molar ratio of the organic acid to the sulfuric acid is from about 4:1 to about 1:1.

The reaction medium generally will comprise about 0.1 moles/L to about 2.0 moles/L of the compound or salt of Formula (III). In one embodiment, the reaction medium comprises about 0.2 moles/L to about 1.7 moles/L of the compound or salt of Formula (III). In one aspect, the reaction medium comprises about 0.3 moles/L to about 1.5 moles/L of the compound or salt of Formula (III). In another aspect, the reaction medium comprises about 0.4 moles/L to about 1.3 moles/L of the compound or salt of Formula (III).

In one illustrative embodiment:
the reaction medium comprises at least about 7 molar equivalents of the organic acid per mole of the compound or salt of Formula (III);
the reaction medium comprises at least about 2.5 molar equivalents of the sulfuric acid per mole of the compound or salt of Formula (III); and
the reaction medium comprises at least about 2.5 moles of the organic acid per mole of the sulfuric acid.

In another illustrative embodiment:
the reaction medium comprises from about 7 molar equivalents to about 9 molar equivalents of the organic acid per mole of the compound or salt of Formula (III);
the reaction medium comprises from about 2 molar equivalents to about 4 molar equivalents of the sulfuric acid per mole of the compound or salt of Formula (III); and
the reaction medium comprises about 0.4 moles/L to about 1.3 moles/L of the compound or salt of Formula (III).

In another illustrative embodiment:
the reaction medium comprises from about 7 molar equivalents to about 9 molar equivalents of the organic acid per mole of the compound or salt of Formula (III);
the reaction medium comprises from about 2 molar equivalents to about 4 molar equivalents of the sulfuric acid per mole of the compound or salt of Formula (III); and
the molar ratio of the organic acid to the sulfuric acid is from about 4:1 to about 1:1.

ii. Compound of Formula (III) Added to Initial Medium

In alternative embodiments, at least a portion, substantially the entire amount, or the entire amount of the compound or salt of Formula (III) is added to the reaction medium during the course of the process rather than the entire amount being present in the initial reaction medium prior to the introduction of the diazotizing agent. In such embodiments, the initial reaction medium (i.e., the reaction medium prior to the introduction of the diazotizing agent) may comprise sulfuric acid alone (i.e., in the absence of the organic acid), the organic acid alone (i.e., in the absence of sulfuric acid), or a combination of sulfuric acid and the organic acid, with any additional amounts of sulfuric acid and/or the organic acid for the reaction medium being introduced with the compound or salt of Formula (III) (e.g., a solution comprising the compound or salt of Formula (III) and the organic acid) or the diazotizing agent (e.g., a solution comprising the diazotizing agent and sulfuric acid). In one aspect, the initial reaction medium comprises sulfuric acid in the absence of the organic acid. In another aspect, the initial reaction medium comprises the organic acid in the absence of sulfuric acid. In another aspect, the initial reaction medium comprises sulfuric acid and the organic acid.

When a portion, substantially the entire amount, or the entire amount of the compound or salt of Formula (III) is added to the reaction medium during the course of the process, substantially the same amounts, ratios, and concentrations that were described above for the reagents and reaction medium are applicable, but should be interpreted to reflect the total amount of the component charged to the reaction medium over the course of the process (e.g., the amount of the compound or salt of Formula (III) present in the initial reaction medium plus the amount of the compound or salt of Formula (III) added to the reaction medium during the course of the process) rather than just the amount of the component initially present in the reaction medium prior to the introduction of the diazotizing agent. Example 15 below provides an example of this approach.

In one embodiment, the compound or salt of Formula (III) is added to the reaction medium with the diazotizing agent. In one aspect, the compound or salt of Formula (III) and the diazotizing agent are added separately to the reaction medium with the diazotizing agent introduced through subsurface addition. The compound or salt of Formula (III) and the diazotizing agent generally are added to the reaction medium concurrently and/or in a manner that substantially avoids generating a significant excess of either of those reagents in the reaction medium. In one aspect, the compound or salt of Formula (III) and the diazotizing agent are added to the reaction medium concurrently. In another aspect, the compound or salt of Formula (III) and the diazotizing agent are added to the reaction medium in a manner that substantially avoids generating a significant excess of either of those reagents in the reaction medium. In another aspect, the compound or salt of Formula (III) and the diazotizing agent are added to the reaction medium concurrently and in a manner that substantially avoids generating a significant excess of either of those reagents in the reaction medium. In another aspect, the rate of addition of each reagent is controlled to maintain a molar ratio of about 1:1 during the addition. Avoiding an excess of either reagent in the reaction medium during the addition can help to maintain a low viscosity reaction mixture, reduce reactor solids, and/or reduce byproduct formation.

In one embodiment, the process comprises concurrently introducing the diazotizing agent, the organic acid, and the compound or salt of Formula (III) into the reaction medium. In one aspect, the process comprises concurrently introducing the diazotizing agent and a solution comprising the organic acid and the compound or salt of Formula (III) into the reaction medium. In another aspect, the reaction medium initially comprises (i.e., comprises before the addition of any diazotizing agent) sulfuric acid in the absence of the organic acid. In another aspect, the reaction medium initially comprises sulfuric acid in the absence of the compound or salt of Formula (III). In another aspect, the reaction medium initially comprises sulfuric acid in the absence of the organic acid and the compound or salt of Formula (III). In another aspect, the reaction medium comprises sulfuric acid and the organic acid in the absence of the compound or salt of Formula (III).

The compound or salt of Formula (III) used in the preparation of the reaction medium, or added to the reaction medium during the process, typically does not require fine milling and can even be added to the reaction medium as an unmilled solid. In one embodiment, the compound or salt of Formula (III) used in the preparation of the reaction medium is provided as a solid having a $D_{90}$ particle size greater than about 150 microns. In another embodiment, the compound or salt of Formula (III) used in the preparation of the reaction medium is provided as an unmilled solid.

B. Diazotizing Agent

The diazotizing agent can be introduced into the reaction medium, for example, as an alkali metal nitrite, nitrous acid, or nitrosylsulfuric acid. In one embodiment, the diazotizing agent is introduced into the reaction medium as an alkali metal nitrite, particularly sodium nitrite. In one embodiment, the diazotizing agent is selected from the group consisting of sodium nitrite and calcium nitrite. In another embodiment, the diazotizing agent is introduced into the reaction medium as sodium nitrite. In another embodiment, the diazotizing agent is introduced into the reaction medium as calcium nitrite. In another embodiment, the diazotizing agent is introduced into the reaction medium as nitrous acid. In another embodiment, the diazotizing agent is introduced into the reaction medium as nitrosylsulfuric acid.

As previously discussed with respect to sodium nitrite, an alkali metal nitrite introduced into the reaction medium reacts with the sulfuric acid present to generate nitrous acid, the nitrous acid generated then reacts with the sulfuric acid present to generate nitrosylsulfuric acid, and the nitrosylsulfuric acid then reacts with the compound or salt of Formula (III) to generate the compound or salt of Formula (IV). The main objective is to introduce the nitrite to the reaction medium in a manner that results in the conversion of the nitrite to nitrous acid which can then react with sulfuric acid to generate nitrosylsulfuric acid.

When an alkali metal nitrite is introduced into the reaction medium as the diazotizing agent, it can be introduced in various forms. In one embodiment, the alkali metal nitrite added to the reaction medium as a solid. Addition as a solid, however, increases the difficulty of maintaining a controlled and consistent addition of the nitrite.

In another embodiment, the alkali metal nitrite is added to the reaction medium as an aqueous solution comprising the alkali metal nitrite. In one aspect, the aqueous solution comprising the alkali metal nitrite is added drop wise to the reaction medium. In another aspect, the aqueous solution comprising the alkali metal nitrite is introduced into the reaction medium through subsurface addition. In another aspect, the alkali metal nitrite is selected from the group consisting of sodium nitrite and calcium nitrite. In another aspect, alkali metal nitrite is sodium nitrite. In another aspect, the alkali metal nitrite is calcium nitrite.

In another embodiment, the alkali metal nitrite is added to the reaction medium as a solution of the alkali metal nitrite in sulfuric acid. In one aspect, the solution of the alkali metal nitrite in sulfuric acid is added drop wise to the reaction medium. In another aspect, the solution of the alkali metal nitrite in sulfuric acid is introduced into the reaction medium through subsurface addition. In another aspect, the alkali metal nitrite is selected from the group consisting of sodium nitrite and calcium nitrite. In another aspect, alkali metal nitrite is sodium nitrite. In another aspect, the alkali metal nitrite is calcium nitrite.

The diazotization reaction proceeds quickly once the diazotizing agent is introduced into the reaction medium and higher temperatures are not required to drive the diazotization reaction to completion. In one embodiment, the reaction medium has a temperature less than or equal to about 25° C. when the diazotizing agent is introduced. In one aspect, the reaction medium has a temperature less than or equal to about 10° C. when the diazotizing agent is introduced. In another aspect, the reaction medium has a temperature from about 0° C. to about 25° C. when the diazotizing agent is introduced. In another aspect, the reaction medium has a temperature from about 0° C. to about 20° C. when the diazotizing agent is introduced. In another aspect, the reaction medium has a temperature from about 0° C. to about 15° C. when the diazotizing agent is introduced. In another aspect, the reaction medium has a temperature from about 0° C. to about 10° C. when the diazotizing agent is introduced. In another aspect, the reaction medium has a temperature from about 10° C. to about 25° C. when the diazotizing agent is introduced. In another aspect, the reaction medium has a temperature from about 5° C. to about 15° C. when the diazotizing agent is introduced.

Although smaller or larger amounts of the diazotizing agent can be employed for the diazotization reaction, a suitable amount generally will be at least about 0.9 molar equivalents. A stoichiometric excess of the diazotizing agent generally will provide a better conversion of the compound or salt of Formula (III) to the compound or salt of Formula (IV), but the stoichiometric excess need not be a large stoichiometric excess. In one embodiment, at least a 0.9 molar equivalent amount of the diazotizing agent per mole of the compound or salt of Formula (III) is introduced into the reaction medium. In one aspect, at least a molar equivalent amount of the diazotizing agent per mole of the compound or salt of Formula (III) is introduced into the reaction medium. In another aspect, about 0.9 molar equivalents to about 1.5 molar equivalents of the diazotizing agent per mole of the compound or salt of Formula (III) is introduced into the reaction medium. In another aspect, about 1.0 molar equivalent to about 1.5 molar equivalents of the diazotizing agent per mole of the compound or salt of Formula (III) is introduced into the reaction medium. In another aspect, about 1.0 molar equivalent to about 1.2 molar equivalents of the diazotizing agent per mole of the compound or salt of Formula (III) is introduced into the reaction medium. In another aspect, about 1.05 molar equivalents of the diazotizing agent per mole of the compound or salt of Formula (III) are introduced into the reaction medium. In another aspect, about 1.05 molar equivalents of sodium nitrite per mole of the compound or salt of Formula (III) are introduced into the reaction medium through subsurface addition.

As previously described above, a portion, substantially the entire amount, or the entire amount of the compound or salt of Formula (III) can be added to the reaction medium during the course of the process rather than being present in the initial reaction medium prior to the introduction of the diazotizing agent. The same process conditions generally apply regardless of whether the diazotizing agent is introduced into a reaction medium containing substantially all of the compound or salt of Formula (III) to be charged to the process or the diazotizing agent and at least a portion of the compound or salt of Formula (III) to be charged to the process are introduced into the reaction medium. When the compound or salt of Formula (III) is added to the reaction medium during the course of the process, however, it generally is beneficial to introduce the compound or salt of Formula (III) and the diazotizing agent to the reaction medium concurrently and in a manner that avoids generating a significant excess of either of those reagents in the reaction medium. In one aspect, the rate of addition of each reagent is controlled such that about 0.9 molar equivalent to about 1.5 molar equivalents of diazotizing agent are added per mole of the compound or salt of Formula (III) added. In another aspect, the rate of addition of each reagent is controlled such that about 1.0 molar equivalent to about 1.5 molar equivalents of the diazotizing agent are added per mole of the compound or salt of Formula (III) added. In another aspect, the rate of addition of each reagent is controlled such that about 1.0 molar equivalent to about 1.2 molar equivalents of the diazotizing agent are added per mole of the compound or salt of Formula (III) added. In another aspect, the rate of addition of each reagent is controlled such that about 1.0 molar equivalent to about 1.05 molar equivalents of the diazotizing agent are added per mole of the compound or salt of Formula (III) added. In another aspect, the rate of addition of each reagent is controlled such that about 1.0 molar equivalent of the diazotizing agent is added per mole of the compound or salt of Formula (III) added. In one aspect, the compound or salt of Formula (III) and the diazotizing agent are added separately to the reaction medium with the diazotizing agent introduced through subsurface addition.

In one embodiment, the diazotizing agent and the compound or salt of Formula (III) are separately introduced into the reaction medium as a first solution comprising the diazotizing agent, and a second solution comprising acetic acid and the compound or salt of Formula (III). In one aspect, the first solution and the second solution are introduced into the reaction medium in a substantially concurrent manner. In another aspect, the first solution is an aqueous solution comprising an alkali metal nitrite, and the second solution comprises acetic acid and the compound or salt of Formula (III). In another aspect, the first solution comprises an alkali metal nitrite and sulfuric acid, and the second solution comprises acetic acid and the compound or salt of Formula (III). In another aspect, the first solution comprises nitrosyl sulfuric acid, and a second solution comprises acetic acid and the compound or salt of Formula (III).

As discussed above, the improved process provides a suitable conversion of the compound or salt of Formula (III) to the compound or salt of Formula (IV). In one embodiment, the percent conversion of the compound or salt of Formula (III) to the compound or salt of Formula (IV) is at least about 80%. In one aspect, the percent conversion of the compound or salt of Formula (III) to the compound or salt of Formula (IV) is at least about 85%. In another aspect, the percent conversion of the compound or salt of Formula (III) to the compound or salt of Formula (IV) is at least about 90%. In another aspect, the percent conversion of the compound or salt of Formula (III) to the compound or salt of Formula (IV) is at least about 95%.

C. Quenching of Diazotizing Agent

Where the diazotizing agent is an alkali metal nitrite (e.g., sodium nitrite or calcium nitrite), nitrosylsulfuric acid, or otherwise results in an excess of nitrous acid being present in the medium, it can be beneficial to add a sufficient amount of a quenching agent to the reaction mixture comprising the 2,5-dichlorobenzenediazonium in order to decompose any excess nitrous acid remaining prior to converting the 2,5-dichlorobenzenediazonium to the 2,5-dichlorophenol. If excess nitrous acid is present during the hydroxylation step described below, for example, under the elevated temperatures of the hydroxylation step the nitrous acid can react with the 2,5-dichlorophenol generated.

In one embodiment of the present disclosure, therefore, the process further comprises adding a quenching agent to the diazonium product mixture in an amount sufficient to decompose any remaining diazotizing agent prior to the subsequent hydrolyzing step. In one aspect, the quenching agent is selected from the group consisting of urea and sulfamic acid. In another aspect, the quenching agent is urea. In another aspect, the quenching agent is sulfamic acid. The reaction pathways for decomposition of nitrous acid when the quenching agent is either urea (1) or sulfamic acid (2) are shown in Scheme 4 below.

Scheme 4

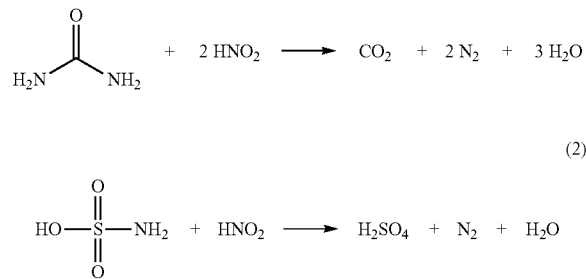

III. Hydroxylation Of 2,5-Dichlorobenzenediazonium

As previously noted, the 2,5-dichlorobenzenediazonium prepared as described above can be hydrolyzed to provide the corresponding 2,5-dichlorophenol, a key intermediate used in the manufacture of dicamba.

Accordingly, in one embodiment, the present disclosure relates to a process for the preparation of a compound corresponding in structure to Formula (V):

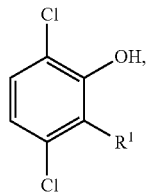
(V)

or a salt thereof, the process comprising:

contacting a compound corresponding in structure to Formula (III):

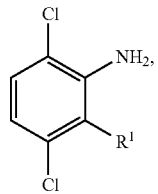
(III)

or a salt thereof, with a diazotizing agent in a reaction medium comprising sulfuric acid and an organic acid selected from the group consisting of $C_2$-$C_6$-alkanoic acids and halo-$C_1$-$C_6$-alkanoic acids to generate a diazonium product mixture comprising the compound or salt of Formula (IV):

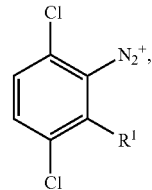
(IV)

or a salt thereof; and hydrolyzing the compound or salt of Formula (IV) to generate a phenol product mixture comprising the compound or salt of Formula (V);

wherein:

$R^1$ is selected from the group consisting of hydrogen, halogen, cyano, —$CH_3$, —$CH_2OH$, —$C(O)R^2$, —$C(O)OR^3$, and —$B(R^4)_2$;

$R^2$ is selected from the group consisting of hydrogen, $C_1$-$C_6$-alkyl, and —$NR^AR^B$; wherein $R^A$ and $R^B$ are independently selected from the group consisting of hydrogen and $C_1$-$C_6$-alkyl; and $R^3$ is selected from the group consisting of hydrogen and $C_1$-$C_6$-alkyl; and $R^4$ is selected from the group consisting of hydroxy and $C_1$-$C_6$-alkyl.

In one aspect, $R^1$ is hydrogen (i.e., the compound of Formula (III) is 2,5-dichloroanaline). In another aspect, $R^1$ is selected from the group consisting of halogen, cyano, —$CH_3$, —$CH_2OH$, —$C(O)R^2$, —$C(O)OR^3$, and —$B(R^4)_2$; and $R^2$, $R^3$, and $R^4$ are as defined above (i.e., the compound of Formula (III) is a 2,5-dichloroanaline compound that is further substituted at the 3-position of the ring).

In one embodiment, the present disclosure relates to a process for the preparation of a compound corresponding in structure to Formula (V):

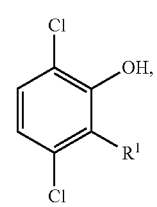
(V)

or a salt thereof, the process comprising:

forming a reaction medium comprising sulfuric acid; an organic acid selected from the group consisting of $C_2$-$C_6$-alkanoic acids and halo-$C_1$-$C_6$-alkanoic acids; and, optionally, a first amount of a compound corresponding in structure to Formula (III):

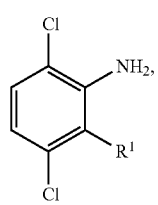
(III)

or a salt thereof;

introducing into the reaction medium a second amount of the compound or salt of the compound of Formula (III), and a diazotizing agent, to generate a diazonium product mixture comprising the compound or salt of Formula (IV);

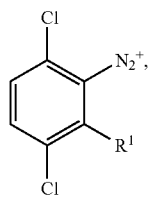

(IV)

or a salt thereof; and hydrolyzing the compound or salt of Formula (IV) to generate a phenol product mixture comprising the compound or salt of Formula (V);

wherein:

$R^1$ is selected from the group consisting of hydrogen, halogen, cyano, —$CH_3$, —$CH_2OH$, —$C(O)R^2$, —$C(O)OR^3$, and —$B(R^4)_2$;

$R^2$ is selected from the group consisting of hydrogen, $C_1$-$C_6$-alkyl, and —$NR^AR^B$; wherein $R^A$ and $R^B$ are independently selected from the group consisting of hydrogen and $C_1$-$C_6$-alkyl; and $R^3$ is selected from the group consisting of hydrogen and $C_1$-$C_6$-alkyl; and $R^4$ is selected from the group consisting of hydroxy and $C_1$-$C_6$-alkyl.

In one aspect, $R^1$ is hydrogen (i.e., the compound of Formula (III) is 2,5-dichloroanaline). In another aspect, $R^1$ is selected from the group consisting of halogen, cyano, —$CH_3$, —$CH_2OH$, —$C(O)R^2$, —$C(O)OR^3$, and —$B(R^4)_2$; and $R^2$, $R^3$, and $R^4$ are as defined above (i.e., the compound of Formula (III) is a 2,5-dichloroanaline compound that is further substituted at the 3-position of the ring).

In one embodiment, the present disclosure relates to a process for the preparation of a compound corresponding in structure to Formula (V):

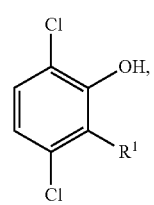

(V)

or a salt thereof, the process comprising:

forming a reaction medium comprising sulfuric acid; an organic acid selected from the group consisting of $C_2$-$C_6$-alkanoic acids and halo-$C_1$-$C_6$-alkanoic acids; and a compound corresponding in structure to Formula (III):

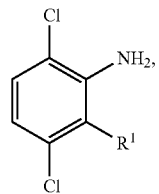

(III)

or a salt thereof; and introducing into the reaction medium a diazotizing agent to generate a diazonium product mixture comprising a compound corresponding in structure to Formula (IV):

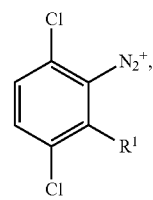

(IV)

or a salt thereof; and hydrolyzing the compound or salt of Formula (IV) to generate a phenol product mixture comprising the compound or salt of Formula (V);

wherein:

$R^1$ is selected from the group consisting of hydrogen, halogen, cyano, —$CH_3$, —$CH_2OH$, —$C(O)R^2$, —$C(O)OR^3$, and —$B(R^4)_2$;

$R^2$ is selected from the group consisting of hydrogen, $C_1$-$C_6$-alkyl, and —$NR^AR^B$; wherein $R^A$ and $R^B$ are independently selected from the group consisting of hydrogen and $C_1$-$C_6$-alkyl; and $R^3$ is selected from the group consisting of hydrogen and $C_1$-$C_6$-alkyl; and $R^4$ is selected from the group consisting of hydroxy and $C_1$-$C_6$-alkyl.

In one aspect, $R^1$ is hydrogen (i.e., the compound of Formula (III) is 2,5-dichloroanaline). In another aspect, $R^1$ is selected from the group consisting of halogen, cyano, —$CH_3$, —$CH_2OH$, —$C(O)R^2$, —$C(O)OR^3$, and —$B(R^4)_2$; and $R^2$, $R^3$, and $R^4$ are as defined above (i.e., the compound of Formula (III) is a 2,5-dichloroanaline compound that is further substituted at the 3-position of the ring).

In one embodiment, the process further comprises adding a quenching agent to the diazonium product mixture in an amount sufficient to decompose any remaining diazotizing agent prior to the hydrolyzing step.

In one embodiment, the process further comprises isolating the compound or salt of Formula (V) from the phenol product mixture.

In one embodiment, the process further comprises recovering the organic acid from the hydrolyzing step and recycling the recovered organic acid to a prior process step.

In one embodiment, the process further comprises recovering the sulfuric acid from the hydrolyzing step and recycling the recovered sulfuric acid to the diazotization and/or hydrolysis process step(s). In one aspect, the recovered sulfuric acid is used to prepare the reaction medium into which the diazotizing agent is introduced to generate the diazonium product mixture comprising the compound or salt of Formula (IV).

In one embodiment, the process further comprises (a) recovering the organic acid from the hydrolyzing step and recycling the recovered organic acid to a prior process step; and (b) recovering the sulfuric acid from the hydrolyzing step and recycling the recovered sulfuric acid to the diazotization and/or hydrolysis process step(s). In one aspect, the recovered sulfuric acid is used to prepare the reaction medium into which the diazotizing agent is introduced to generate the diazonium product mixture comprising the compound or salt of Formula (IV).

Although the compound or salt of Formula (IV) can be isolated from the diazonium product mixture and then hydrolyzed to the compound or salt of Formula (V), such isolation typically is not carried out prior to the hydrolyzing step. In view of the potential instability of isolated diazonium salts, the compound or salt of Formula (IV) generally is hydrolyzed to the compound or salt of Formula (V) in situ in the diazonium product mixture and the compound or salt of Formula (V) recovered from the resulting phenol product mixture.

The compound or salt of Formula (IV) can be hydrolyzed to the compound or salt of Formula (V) through any suitable means. In one embodiment, for example, the compound or salt of Formula (IV) is hydrolyzed by heating the diazonium product mixture to generate a phenol product mixture comprising the compound or salt of Formula (V). In one aspect, the compound or salt of Formula (IV) is subjected to thermal hydrolysis and the resulting compound or salt of Formula (V) is immediately isolated from the remaining diazonium (e.g., through azeotropic steam distillation or extraction into an organic phase present in the reactor) to minimize further reaction between the compound or salt of Formula (V) and the remaining diazonium.

In another embodiment, the compound or salt of Formula (IV) is hydrolyzed by subjecting the diazonium product mixture to steam distillation to generate a phenol product mixture comprising the compound or salt of Formula (V). In one aspect, the diazonium product mixture is maintained at a temperature between about 105° C. to about 200° C. during the steam distillation. In another aspect, the diazonium product mixture is maintained at a temperature between about 130° C. to about 170° C. during the steam distillation. In another aspect, the diazonium product mixture is maintained at a temperature of about 150° C. during the steam distillation. In another aspect, the phenol product mixture resulting from the steam distillation is a distillate comprising the organic acid, water, and the compound or salt of Formula (V). In another aspect, the process further comprises isolating the compound or salt of Formula (V) from the distillate. In another aspect, the process further comprises recovering the organic acid from the distillate and recycling the recovered organic acid to a prior process step.

By way of further illustration, Example 12 below describes the subsurface addition of the diazonium product mixture to hot concentrated sulfuric acid using a syringe pump followed by the introduction of steam into the resulting mixture at a rate sufficient to provide for the azeotropic distillation of the 2,5-dichlorophenol. Although the addition of steam to the sulfuric acid generated an initial exotherm, additional heating (a heating mantle) was supplied as required to maintain the resulting mixture at a temperature of about 150° C. during the steam distillation. The overall yield of the 2,5-dichlorophenol was around 90%.

In another embodiment, the compound or salt of Formula (IV) is hydrolyzed by: (i) combining the diazonium product mixture with an organic solvent to form a biphasic mixture comprising the compound or salt of Formula (IV); and (ii) heating the biphasic mixture to generate a phenol product mixture comprising the compound or salt of Formula (V). In one aspect, the organic solvent comprises one or more xylenes. In another aspect, the biphasic mixture is heated under reflux conditions. In another aspect, the biphasic mixture is refluxed at a temperature from about 95° C. to about 125° C. In another aspect, the biphasic mixture is refluxed at a temperature from about 95° C. to about 125° C. for a period of about 30 minutes to about 500 minutes.

The biphasic mixture upon cooling after refluxing comprises an aqueous phase and an organic phase comprising the compound or salt of Formula (V). The organic phase can be separated from the aqueous phase by conventional means (such as phase separation) to provide a phenol product mixture comprising the compound or salt of Formula (V). The compound or salt of Formula (V) then can be isolated from the phenol product mixture by conventional means (such as evaporation or distillation).

Alternatively, water (e.g., deionized water, etc.) can be used in place of steam to hydrolyze the compound or salt of Formula (V) present in the diazonium product mixture in a manner similar to the various embodiments described above. The water likewise serves as a nucleophile in the hydrolysis reaction and also promotes the azeotropic distillation of the hydrolysis product. Use of water instead of steam potentially can reduce process costs and problems associated with the use of glass-lined equipment. The entire amounts of the diazonium product mixture and water can be charged to a hydrolysis reactor (such as a distillation column, etc.) containing a reaction medium comprising aqueous sulfuric acid at the beginning of the hydrolysis step or, alternatively, at least a portion of the diazonium product mixture and a portion of the water can be added to the reaction medium during the course of the hydrolysis step.

In one embodiment, at least a portion of the diazonium product mixture and a portion of the water are introduced concurrently into the reaction medium comprising aqueous sulfuric acid over a period of time. During this addition, the resulting reaction medium is maintained at a temperature sufficient to hydrolyze the compound or salt of Formula (III) to the compound or salt of Formula (IV) and achieve the azeotropic distillation of the compound or salt of Formula (IV) from the reaction medium. Suitable distillation conditions are as previously described above. In one aspect, the reaction medium is maintained at a temperature of at least about 150° C. and the additions of the diazonium product mixture and the water to the reaction medium are completed in approximately the same period of time. In another aspect, the reaction medium is maintained at a temperature of about 160° C. Example 16 below provides an example of the concurrent addition of the diazonium product mixture and water to the reaction medium.

In another embodiment, water is added to the reaction medium before the diazonium product mixture is introduced to the reaction medium and, optionally, again after the diazonium product mixture addition to the reaction medium has been completed. In this embodiment, a reaction medium comprising aqueous sulfuric acid is placed in a hydrolysis reactor (such as a distillation column, etc.) and heated. The reaction medium can comprise, for example, a commercially available aqueous sulfuric acid solution, aqueous sulfuric acid recycled from a later stage of the process, or aqueous sulfuric acid prepared from a concentrated sulfuric acid solution (such as by adding the first portion of water to the concentrated sulfuric acid, either before or after the placing the concentrated sulfuric acid in the hydrolysis reactor). The reaction medium is heated to a temperature sufficient to provide for a substantially constant distillation of water in the distillation bridge. A second portion of water and the diazonium product mixture are then concurrently introduced to the reaction medium over a period of time. During this addition, the resulting reaction medium is maintained at a temperature sufficient to hydrolyze the compound or salt of Formula (III) to the compound or salt of Formula (IV) and achieve the azeotropic distillation of the compound or salt of Formula (IV) from the reaction medium. Suitable distillation conditions are as previously described above. Once the addition of the diazonium product mixture is complete, a third portion of water is optionally introduced into the reaction medium and heating is discontinued. In one aspect, the reaction medium is maintained at a temperature of at least about 150° C. and/or the distilling head is maintained at a temperature of at least about 85° C. In another aspect, the reaction medium is maintained at a temperature of about 160° C. and/or the distilling head is maintained at a temperature of about 90° C. Example 16 below provides an example of this approach.

IV. Recycling of Organic Acid

As mentioned above, the process may further comprise recovering the organic acid from the hydrolyzing step and recycling the recovered organic acid to a prior process step.

V. Recycling of sulfuric acid

As mentioned above, the process may further comprise recovering the sulfuric acid from the hydrolyzing step and recycling the recovered sulfuric acid to a prior process step. For example, the process can further comprise recovering sulfuric acid from the hydrolyzing step and recycling the recovered sulfuric acid to the diazotization and/or hydrolysis process step(s). In one aspect, the recovered sulfuric acid is used to prepare the reaction medium into which the diazotizing agent is introduced to generate the diazonium product mixture comprising the compound or salt of Formula (IV). In another aspect, the recovered sulfuric acid is used to prepare the reaction medium into which the diazonium product mixture is hydrolyzed to generate a phenol product mixture comprising the compound or salt of Formula (V). Such recycling can reduce the sulfuric acid requirements of, and costs associated with, the process.

VI. Reduction of the Compound of Formula (Ii)

In one embodiment, the process further comprises the step of reducing a compound corresponding in structure to Formula (II):

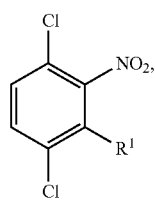

(II)

or a salt thereof, to generate a compound corresponding in structure to Formula (III):

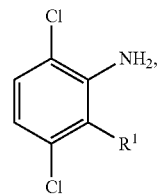

(III)

or a salt thereof.

wherein:

$R^1$ is selected from the group consisting of hydrogen, halogen, cyano, —$CH_3$, —$CH_2OH$, —$C(O)R^2$, —$C(O)OR^3$, and —$B(R^4)_2$;

$R^2$ is selected from the group consisting of hydrogen, $C_1$-$C_6$-alkyl, and —$NR^A R^B$; wherein $R^A$ and $R^B$ are independently selected from the group consisting of hydrogen and $C_1$-$C_6$-alkyl; and $R^3$ is selected from the group consisting of hydrogen and $C_1$-$C_6$-alkyl; and $R^4$ is selected from the group consisting of hydroxy and $C_1$-$C_6$-alkyl.

In one aspect, $R^1$ is hydrogen (i.e., the compound of Formula (II) is 1,4-dichloronitrobenzene). In another aspect, $R^1$ is selected from the group consisting of halogen, cyano, —$CH_3$, —$CH_2OH$, —$C(O)R^2$, —$C(O)OR^3$, and —$B(R^4)_2$; and $R^2$, $R^3$, and $R^4$ are as defined above (i.e., the compound of Formula (II) is a 1,4-dichloronitrobenzene compound that is further substituted at the 3-position of the ring).

The reducing step can be carried out in any suitable manner such as, for example, contacting the compound or salt of Formula (II) with hydrogen in the presence of a suitable catalyst to generate the compound or salt of Formula (III). In one aspect, the reducing step is conducted in a solvent comprising the same organic acid that is used in the diazotizing step. In another aspect, the reducing step is conducted in a solvent comprising the same organic acid that is used in the diazotizing step, and the process comprises recovering the organic acid from the hydrolyzing step and recycling the recovered organic acid to the reducing step.

In one illustrative embodiment, the process further comprises a reducing step in which 1,4-dichloronitrobenzene is converted to 2,5-chloroaniline as shown in Scheme 5 below.

Scheme 5

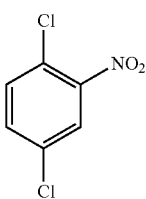 reduction 1,4 Dichloronitrobenzene
(1,4-DCNB)

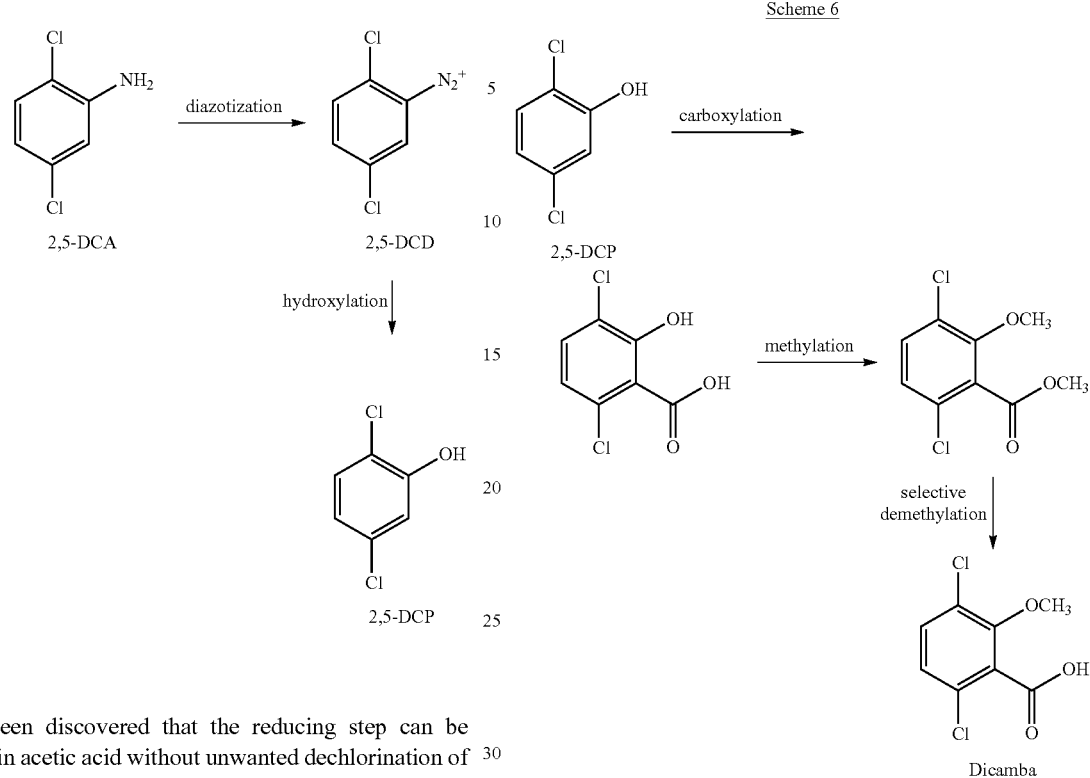

Scheme 6

It has been discovered that the reducing step can be conducted in acetic acid without unwanted dechlorination of the 2,5-dichloroaniline product occurring. Upon completion of hydrogenation of the 1,4-dichloronitrobenzene, the acetic acid reaction mixture comprising the resulting 2,5-dichloroaniline can be directly transferred into the diazonium reactor. The direct transfer eliminates the need to isolate and purify the 2,4-dichloroaniline and the related solvent and equipment requirements. During the diazotizing step, this procedure avoids the use of a mill to assist with the solubility of 2,5-dichloroaniline and reduces the amount of sulfuric acid needed during the course of the reaction. An additional benefit of using the acetic acid is realized during the later distillation purification of 2,5-dichlorophenol in which the acetic acid prevents plugging of the distillation apparatus. The acetic acid additionally can be recovered and recycled back into the process simplifying the overall synthetic sequence and reducing waste.

VII. Conversion of 2,5-Dichlorophenol to Dicamba

As previously noted, the 2,5-dichlorophenol prepared as described above is a key intermediate used in the manufacture of dicamba. A number of synthetic routes for converting 2,5-dichlorophenol to dicamba have been reported in the literature and any such suitable route may be employed. For example, many of the reported routes generally involve the following process steps: (i) carboxylating the 2,5-dichlorophenol to provide 2-hydroxy-3,6-dichloro-benzoic acid (e.g., carboxylation using a Kolbe-Schmidtt Reaction), (ii) methylating the 2-hydroxy-3,6-dichloro-benzoic acid to provide methyl 3,6-dichloro-2-methoxybenzoate (e.g., methylation by treatment with dimethyl sulfate, dimethyl carbonate, or methyl chloride), and (iii) selectively demethylating the ester group of the methyl 3,6-dichloro-2-methoxybenzoate to provide dicamba (e.g., saponification) as shown in Scheme 6 below:

Among the various literature references reporting synthetic methods for preparing dicamba or dicamba intermediates, for example, are the following:

(1) U.S. Pat. No. 3,013,054 reports a process for preparing dicamba that proceeds through a 2,5-dichlorophenol intermediate.
(2) Zhang, et al., "Synthesis of Herbicide Dicamba," Nongyao 2002, 41 (11), 13-14 (Ch.), reports a process for the preparation of dicamba from 2-5-dichloroaniline that proceeds through a 2,5-dichlorophenol intermediate.
(3) Zhang, et al., "Study on the Preparation of Dicamba," Nongyao 2002, 41 (7), 15-17 (Ch.), reports a three-step process for the preparation of dicamba from 2,5-dichlorophenol.
(4) Eckstein, et al., Przem. Chem. 1979, 58 (10), 533-536 (Pol.), reports a process for preparing dicamba from a 2,5-dichlorophenol sodium salt.
(5) U.S. Pat. No. 3,345,157 reports a process for methylating 2-hydroxy-3,6-dichloro-benzoic acid to provide dicamba.
(6) Matyakh, et al., "2-Methoxy-3,6-dichloro-benzoic acid," Otkrytiya, Izobret. Prom. Obraztsy, Tovarnye, Znake 1973, 50 (18), 177-178, reports a process for methylating a 2-hydroxy-3,6-dichloro-benzoic acid sodium salt to provide dicamba.
(7) Zhang, et al., "Study on the 0-Alkylation for 3,6-dichlorosalicylic Acid by Chloromethane," Huangong Shikan 2002, 16 (12) 45-48 (Ch.), reports the O-alkylation of 2-hydroxy-3,6-dichloro-benzoic acid to provide dicamba.
(8) CN102942474A report a process via carboxylation of 2,5-dichlorophenol and methylation of 3,6-dichlorosalicylic acid with chloromethane to provide dicamba.
(9) CN102125035B reports a process involving carboxylation of 2,5-dichlorophenol and methylation of 3,6-dichlorosalicylic acid with dimethyl carbonate to provide dicamba.

(10) CN1830942A reports a process involving methylation of 3,6-dichlorosalicylic acid with dimethyl sulfate to provide dicamba.

Accordingly, in one embodiment, the present disclosure relates to a process for the preparation of dicamba, i.e., a compound corresponding in structure to Formula (VI):

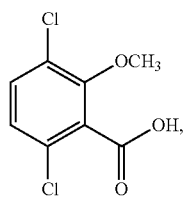
(VI)

or a salt thereof, wherein the process comprises converting a compound prepared as disclosed in this specification and corresponding in structure to Formula (V-a):

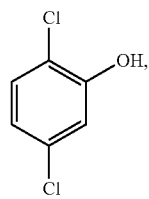
(V-a)

or a salt thereof, to the compound of Formula (VI).

In one embodiment, the present disclosure relates to a process for the preparation of dicamba, i.e., a compound corresponding in structure to Formula (VI):

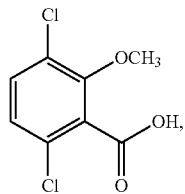
(VI)

or a salt thereof, the process comprising:

contacting a compound corresponding in structure to Formula (III-a):

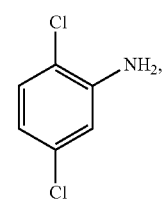
(III-a)

or a salt thereof, with a diazotizing agent in a reaction medium comprising sulfuric acid and an organic acid selected from the group consisting of $C_2$-$C_6$-alkanoic acids and halo-$C_1$-$C_6$-alkanoic acids to generate a diazonium product mixture comprising a compound corresponding in structure to Formula (IV-a):

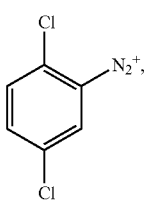
(IV-a)

or a salt thereof;

hydrolyzing the compound or salt of Formula (IV-a) to generate a phenol product mixture comprising a compound corresponding in structure to Formula (V-a):

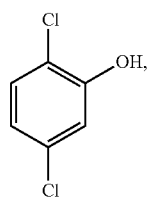
(V-a)

or a salt thereof;

carboxylating the compound or salt of Formula (V-a) to generate a carboxylated product mixture comprising a compound corresponding in structure to Formula (V-b):

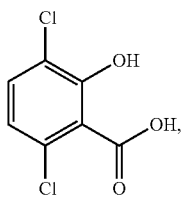
(V-b)

or a salt thereof; and converting the compound or salt of Formula (V-b) to the compound or salt of Formula (VI).

In one aspect, the converting step comprises methylating the compound or salt of Formula (V-b) to generate a methylated product mixture comprising a compound corresponding in structure to Formula (V-c):

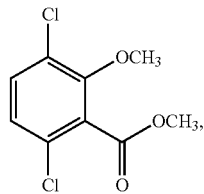
(V-c)

or a salt thereof; and selectively demethylating the compound or salt of Formula (V-c) to generate a dicamba product mixture comprising the compound or salt of Formula (VI). In another aspect, the converting step comprises selectively methylating the compound or salt of Formula (V-b) to generate a dicamba product mixture comprising the compound or salt of Formula (VI).

In one embodiment, the present disclosure relates to a process for the preparation of dicamba, i.e., a compound corresponding in structure to Formula (VI):

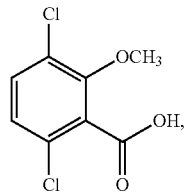
(VI)

or a salt thereof, the process comprising:

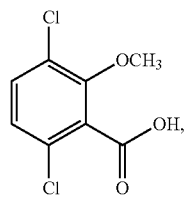
(VI)

or a salt thereof, the process comprising:

forming a reaction medium comprising sulfuric acid; an organic acid selected from the group consisting of $C_2$-$C_6$-alkanoic acids and halo-$C_1$-$C_6$-alkanoic acids; and, optionally, a first amount of a compound corresponding in structure to Formula (III-a):

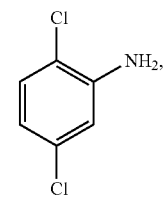
(III-a)

or a salt thereof;

introducing into the reaction medium a second amount of the compound or salt of the compound of Formula (III), and a diazotizing agent, to generate a diazonium product mixture comprising a compound corresponding in structure to Formula (IV-a):

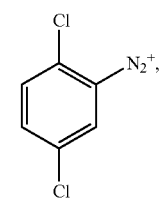
(IV-a)

or a salt thereof;

hydrolyzing the compound or salt of Formula (IV-a) to generate a phenol product mixture comprising a compound corresponding in structure to Formula (V-a):

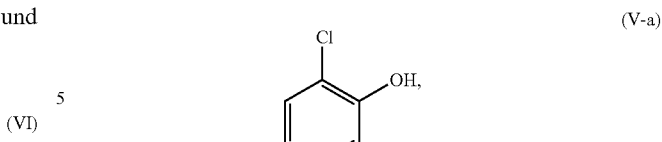
(V-a)

or a salt thereof; and carboxylating the compound or salt of Formula (V-a) to generate a carboxylated product mixture comprising a compound corresponding in structure to Formula (V-b):

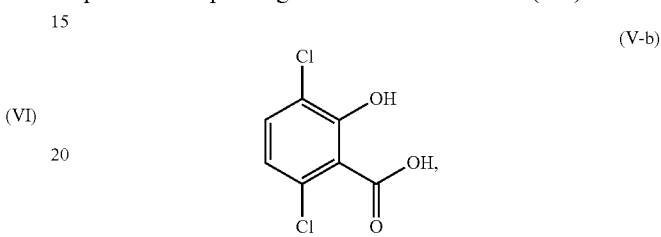
(V-b)

or a salt thereof; and converting the compound or salt of Formula (V-b) to the compound or salt of Formula (VI).

In one aspect, the converting step comprises methylating the compound or salt of Formula (V-b) to generate a methylated product mixture comprising a compound corresponding in structure to Formula (V-c):

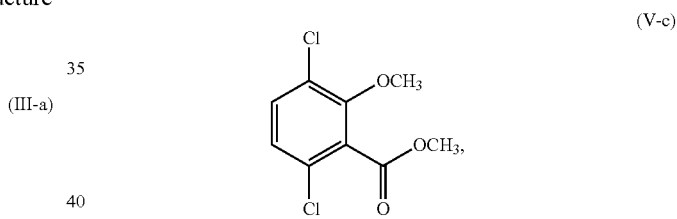
(V-c)

or a salt thereof; and selectively demethylating the compound or salt of Formula (V-c) to generate a dicamba product mixture comprising the compound or salt of Formula (VI). In another aspect, the converting step comprises selectively methylating the compound or salt of Formula (V-b) to generate a dicamba product mixture comprising the compound or salt of Formula (VI).

In one embodiment, the present disclosure relates to a process for the preparation of dicamba, i.e., a compound corresponding in structure to Formula (VI):

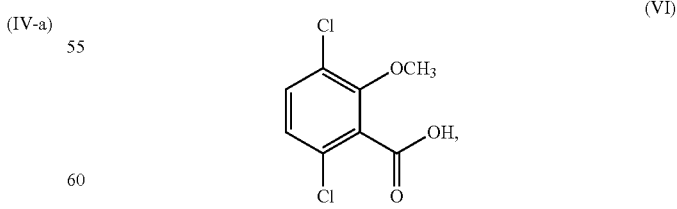
(VI)

or a salt thereof, the process comprising:

forming a reaction medium comprising sulfuric acid; an organic acid selected from the group consisting of $C_2$-$C_6$-alkanoic acids and halo-$C_1$-$C_6$-alkanoic acids; and a compound corresponding in structure to Formula (III-a):

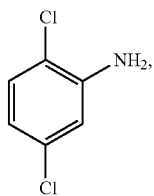
(III-a)

or a salt thereof;

introducing into the reaction medium a diazotizing agent to generate a diazonium product mixture comprising a compound corresponding in structure to Formula (IV-a):

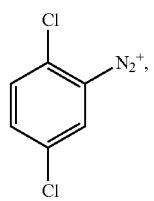
(IV-a)

or a salt thereof;

hydrolyzing the compound or salt of Formula (IV-a) to generate a phenol product mixture comprising a compound corresponding in structure to Formula (V-a):

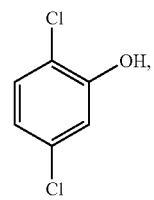
(V-a)

or a salt thereof;

carboxylating the compound or salt of Formula (V-a) to generate a carboxylated product mixture comprising a compound corresponding in structure to Formula (V-b):

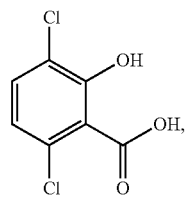
(V-b)

or a salt thereof; and converting the compound or salt of Formula (V-b) to the compound or salt of Formula (VI).

In one aspect, the converting step comprises methylating the compound or salt of Formula (V-b) to generate a methylated product mixture comprising a compound corresponding in structure to Formula (V-c):

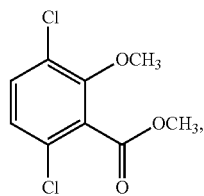
(V-c)

or a salt thereof; and selectively demethylating the compound or salt of Formula (V-c) to generate a dicamba product mixture comprising the compound or salt of Formula (VI). In another aspect, the converting step comprises selectively methylating the compound or salt of Formula (V-b) to generate a dicamba product mixture comprising the compound or salt of Formula (VI).

In one embodiment, the process further comprises isolating the compound or salt of Formula (VI) from the dicamba product mixture.

VIII. EXAMPLES

Example 1

Analytical Methods (2,5-Dichloroaniline and 2,5-Dichlorophenol)

Unless otherwise stated, chromatography was used to monitor the 2,5-dichloroaniline consumed and the 2,5-dichlorophenol produced in the diazotization/hydroxylation reactions discussed in the following examples:

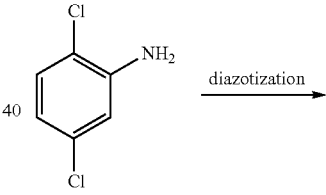

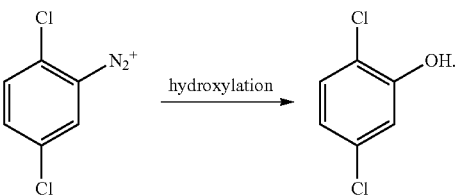

Additional analytical methods used in certain of the examples also are discussed below.

A. Thin Layer Chromatography (TLC) Method

In one analytical method, thin layer chromatography (TLC) was used to monitor the reaction. For example, TLC using a mobile phase of dichloromethane, hexane, and methanol in a ratio of 20 to 75 to 5, respectively, gave a retention factor for 2,5-dichloroaniline of about 0.5 and a retention factor for 2,5-dichlorophenol of about 0.3. 2,5-Dichlorophenol exhibited a yellow spot when developed with potassium permanganate stain. 2,5-Dichloroaniline exhibited a blue spot when developed with cerium-ammonium-molybdate (CAM) stain. 2,5-Dichlorobenzene diazonium, however, stayed at the baseline of the plate. Disappearance of the 2,5-dichloroaniline spot on TLC generally indicated that the 2,5-dichloroaniline had been converted to the 2,5-dichlorobenzene diazonium.

B. HPLC Method

In another analytical method, HPLC was used to monitor the reaction. HPLC was conducted on an Agilent 1260 Infinity Analytical-Scale LC/MS Purification System equipped with a diode array UV detector and monitored at 280 nm. The column was an Agilent Poroshell 120 C-18EC, 4.6×50 mm, 2.7 micron with a pre-column filter. The HPLC was conducted at a flow rate of 2 mL/minute of mobile phase water (0.1% trifluoroacetic acid) and acetonitrile as described in Table 1-A below:

TABLE 1-A

HPLC Method

| TIME | % WATER | % ACETONITRILE |
| --- | --- | --- |
| 0.00 | 70 | 30 |
| 0.25 | 70 | 30 |
| 4.00 | 5 | 95 |
| 4.25 | 70 | 30 |
| 5.00 | 70 | 30 |

The retention times shown in Table 1-B below were observed:

TABLE 1-B

HPLC Retention Times

| TIME | COMPOUND |
| --- | --- |
| 0.3 minutes | 2,5-dichlorobenzene diazonium sulfate |
| 0.7 minutes | 3-chloroaniline |
| 1.9 minutes | 2,5-dichlorophenol |
| 2.2 minutes | 2,5-dichloroaniline |
| 2.5 minutes | 1,4-dichloronitrobenze |
| 2.9 minutes | 1,4-dichlorobenzene |

Disappearance of the 2,5-dichloroaniline peak on HPLC generally indicated that the 2,5-dichloroaniline had been converted to the 2,5-dichlorobenzene diazonium.

C. Gas Chromatography Mass Spectroscopy Method

Gas chromatography mass spectroscopy was performed on an Agilent system using a J&W 122-5535 DB-SMS-UI (0.25 mm×0.25 µm×30 m) column. Method: 1 minute hold at 80° C.; 2 to 9 minute gradient 80° C. to 320° C.; 1 minute hold at 320° C. Helium at 54 mL/minute flow, flame ionization detector (FID detector), and 1 µL injection.

D. Nuclear Magnetic Resonance Method

Nuclear magnetic resonance was run on a Brucker 600 MHz instrument. Deuterated solvents from Cambridge Isotope Laboratories, Ltd. including methanol, chloroform and dimethylsulfoxide were used as required.

E. Water Content Method

Percent water by weight determination was run on a Mettler DL18 Karl Fischer instrument using Aqua Star CombiTitrant 5 acquired from EMD Millipore.

Example 2

Analytical Method (2,5-Dichlorobenzene Diazonium)

An analytical method was developed for evaluating the conversion of 2,5-dichloroaniline to 2,5-dichlorobenzene diazonium in the diazotization reaction:

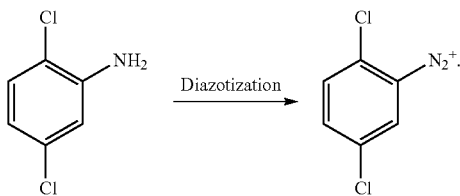

The 2,5-dichlorobenzene diazonium produced was not isolated, but instead was quenched with hypophosphorous acid (H$_3$PO$_2$) and converted to the corresponding 1,4-dichlorobenzene:

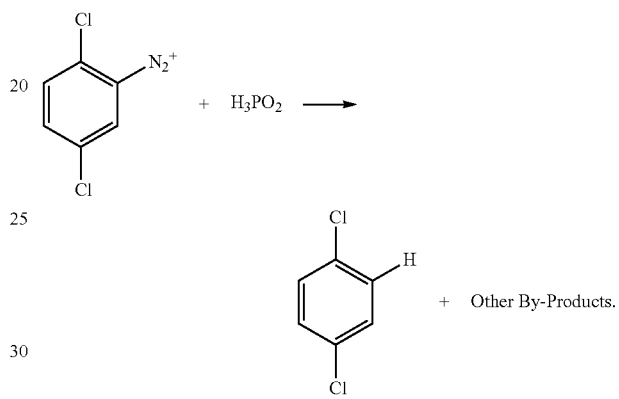

Although the primary product of the conversion was 1,4-dichlorobenzene, it was observed that the hypophosphorous acid reaction produced other minor by-products as detected by HPLC. The amount of 1,4-dichlorobenzene produced was then determined and that value was used to calculate the extent to which the initial amount of the 2,5-dichloroaniline charged to the reaction was converted to the 2,5-dichlorobenzene diazonium.

Specifically, after the reaction medium comprising the 2,5-dichloroaniline was treated with sodium nitrite and warmed to room temperature, an aliquot (approximately 200 mg) of the resulting reaction mixture was weighed into a 10 mL volumetric flask, and a volume of hypophosphorous acid (50% weight/weight solution of hypophosphorous acid/water; approximately 10 times the volume of the reaction mixture aliquot) was added to the flask and the quenched mixture agitated for five minutes at room temperature in a manner similar to the analytical method reported in *J. Org. Chem.* Vol. 42, No. 8, 1977; *J. Am. Chem. Soc.* Vol. 72, No. 7, 1950. The quenched mixture then was diluted with methanol (up to 10 mL) to dissolve any precipitate present and analyzed by HPLC. Response factors were developed for 1,4-dichlorobenzene and used to quantify that compound.

An aliquot of the reaction mixture also can be evaluated without hypophosphorous treatment to measure the remaining 2,5-dichloroaniline using appropriate response factors and then subtracting the measured amount from the initial amount of the 2,5-dichloroaniline charged to the reaction to determine the corresponding amount of 2,5-dichlorobenzene diazonium produced.

Example 3

Diazotization/Hydroxylation in Sulfuric Acid (Biphasic Reflux)

2,5-Dichloroaniline (105 mmol, Sigma Aldrich) was recrystallized from 125 mL of ethanol/water (3/2 volume/volume) to yield fine, off-white crystals of 2,5-dichloroaniline (89.6% yield). In a first experiment, 16.1 g (123 mmol) of a 75% (weight percent) sulfuric acid solution in water was added to 12.3 mmol of the recrystallized 2,5-dichloroaniline in an exothermic reaction that increased the temperature of the resulting mixture to about 60° C. The mixture was stirred vigorously in a 40 mL beaker while the temperature was reduced to about 10 to 20° C. using a cold water bath. Cooling produced a lumpy suspension of the 2,5-dichloroaniline diazonium sulfate salt. A spatula was used to further grind and pulverize the suspension until it the suspension was smooth. Sodium nitrite (910 mg, 13.2 mmol) was added to the suspension in one portion resulting in the evolution of an orange gas ($NO_x$) and producing a heterogeneous mixture. The mixture was stirred at room temperature for one hour. Solid sulfamic acid (80 mg, 0.9 mmol) was added and the mixture stirred for an additional 30 minutes. The viscous and corrosive mixture was then aliquotted into heated xylenes (13.5 mL at about 125° C.) via pipette over a 10 minute period. The mixture was stirred at reflux for 30 minutes. Stirring was stopped and the mixture was allowed to cool to room temperature overnight. While in the reaction vessel, the phases partitioned. The xylene layer was isolated and the 2,5-dichlorophenol yield determined (6.26%) using HPLC response factors. 2,5-Dichloroaniline diazonium and unreacted 2,5-dichloroaniline were detected in the aqueous phase but not quantified.

The low yield suggested that the 2,5-dichloroaniline diazonium did not fully form or the hydrolysis reaction failed. It was hypothesized that poor solubility of the 2,5-dichloroaniline sulfate salt and the 2,5-dichloroaniline diazonium intermediate likely contributed to the low yield of the 2,5-dichlorophenol product. To fully dissolve the 2,5-dichloroaniline and ensure the formation of the sulfate salt, four additional experiments were performed in which the 2,5-dichloroaniline/sulfuric acid solution was heated to 94° C. to provide a homogenous solution. The solution was cooled to about 10° C. to 20° C. and became a heterogeneous mixture. The sodium nitrite then was added piecewise over a 15 minute period. The hydrolysis was performed in xylenes as described above to give yields of the 2,5-dichlorophenol product ranging from 23% to 50% as reported in Table 3-A below:

TABLE 3-A 2,5-Dichlorophenol Yield (Sulfuric Acid/Biphasic Reflux)

| | | | | | |
|---|---|---|---|---|---|
| $NaNO_2$ Equivalents | 1.07 | 1.07 | 1.07 | 1.15 | 1.15 |
| Nitrite Quench | Sulfamic | None | Sulfamic | None | Sulfamic |
| % Unreacted 2,5-DCA | Yes | 5.33% | 8.38% | 3.48% | 0.93% |
| % Yield 2,5-DCP | 6.26% | 49.92% | 23.30% | 44.10% | 28.68% |
| Clean Product Peak* | No | No | No | No | No |

*Refers to the HPLC of the organic phase post-hydrolysis.

Example 4

Diazotization/Hydroxylation in Sulfuric Acid (Distillation)

2,5-Dichloroaniline (8.95 mmol) was added to a reactor containing concentrated sulfuric acid (4 mL) and the mixture was heated to 65° C. to dissolve all of the 2,5-dichloroaniline. The resulting solution was cooled to 2° C. and formed a heterogeneous slurry. A solution of sodium nitrite (9.51 mmol) in sulfuric acid (4 mL) was added to the slurry over a 15 minute period with a maximum temperature of 7° C. being reached. The slurry was slowly warmed to room temperature, a distillation apparatus and receiving flask attached, and the slurry was heated to 157° C. Water (25 mL) was added to the reactor via an addition funnel over a 1.5 hour period. Heating and distillation continued for another 2.5 hours in order to azeotrope the 2,5-dichlorophenol produced and water into the receiving flask.

Upon cooling of the distillate, the 2,5-dichlorophenol product precipitated as a white solid (44% isolated yield of solid product with an additional 4.5% in the distillate that could have been extracted with organic solvent). No by-products formed and unreacted 2,5-dichloroaniline (9%) was recovered in the aqueous phase of the reactor. Formation of the 2,5-dichlorobenzene diazonium again appeared to be hindered by solubility of the 2,5-dichloroaniline in sulfuric acid.

Example 5

Solubility Study

Three different commercially available sources of 2,5-dichloroaniline (Sigma, Acros, and AlfaAesar) were evaluated for solubility in several different solvents under the specific conditions reported in Table 5-A. The 2,5-dichloroaniline obtained from Sigma was evaluated with and without milling. Results from the study are reported in Table 5-A.

In general, the 2,5-dichloroaniline was readily soluble in acetic acid and trifluoroacetic acid at all temperatures. In contrast, it was insoluble in concentrated hydrochloric acid, 75% sulfuric acid (weight/weight sulfuric acid/water), and formic acid at all temperatures tested. Although 2,5-dichloroaniline was soluble in concentrated sulfuric acid at 80° C., solubility at the lower temperatures tested still was limited. Milling the 2,5-dichloroaniline did appear to improve solubility in concentrated sulfuric acid.

When sulfuric acid was added to the milled or unmilled 2,5-dichloroaniline, the 2,5-dichloroaniline clumped up and formed a "crust" on itself. It is hypothesized that this crust is a 2,5-dichloroaniline sulfate salt that forms and creates a salt capsule enclosing the 2,5-dichloroaniline solubility. With vigorous stirring by stir bar or paddle-equipped stir rod, the mixture containing the "crusted" 2,5-dichloroaniline typically can be converted to a slurry of the 2,5-dichloroaniline sulfate salt.

TABLE 5-A 2,5-Dichloroaniline Solubility (Different Solvents/Conditions)

| SOURCE | MILLED? | SOLVENT | MOLARITY | EXOTHERMIC SOLVENT ADDITION | TEMPERATURE 10° C. | 25° C. | 80° C. |
|---|---|---|---|---|---|---|---|
| Sigma | No | Conc. H$_2$SO$_4$ | 2.24 | Yes | Insoluble | Insoluble | Soluble |
| Sigma | No | Conc. HCl | 2.24 | Slight | Insoluble | Insoluble | Insoluble |
| Sigma | No | Glacial Acetic Acid | 2.24 | No | Solvent Froze | Soluble | Soluble |
| Sigma | No | Formic Acid (88%) | 2.24 | No | Insoluble | Insoluble | Insoluble |
| Sigma | No | 75% H$_2$SO$_4$ | 2.24 | Slight | Insoluble | Insoluble | Insoluble |
| Sigma | No | Trifluoracetic Acid | 2.24 | No | Soluble | Soluble | Soluble |
| Acros | No | Conc. H$_2$SO$_4$ | 2.24 | Yes | Partial | Partial | Soluble |
| Acros | No | Glacial Acetic Acid | 2.24 | No | Soluble | Soluble | Soluble |
| Acros | No | Conc. H$_2$SO$_4$ | 1.12 | Yes | Partial | Soluble | Soluble |
| Acros | No | Glacial Acetic Acid | 1.12 | No | Soluble | Soluble | Soluble |
| AlfaAesar | No | Conc. H$_2$SO$_4$ | 1.12 | Yes | Partial | Partial | Soluble |
| AlfaAesar | No | Glacial Acetic Acid | 2.24 | No | Soluble | Soluble | Soluble |
| Sigma | Yes | Conc. H$_2$SO$_4$ | 2.13 | Yes | Soluble | Soluble | — |
| Sigma | Yes | Conc. H$_2$SO$_4$ | 1.16 | Yes | Soluble | Soluble | — |
| Sigma | Yes | Conc. H$_2$SO$_4$ | 0.58 | Yes | Soluble | Soluble | — |
| Sigma | Yes | Glacial Acetic Acid | 1.16 | No | Soluble | Soluble | — |
| Sigma | Yes | Glacial Acetic Acid | 2.24 | No | Soluble | Soluble | — |

Example 6

Diazotization in Acetic Acid

Acetic acid (4 mL) was added to a beaker containing 1.45 g (89.5 mmol) of 2,5-dichloroaniline. The reaction mixture was chilled in an ice bath to 12° C. and sodium nitrite (0.81 g, 11.74 mmol, 1.07 equivalents) in 4 mL water was added via pipette over a period of 30 minutes. An orange gas evolved and the reaction mixture turned thick and orange-yellow. After the addition of the sodium nitrite, the reaction mixture was stirred at 12° C. for 30 minutes. The reaction mixture was stored overnight at room temperature. The mixture was added via pipette over a period of 30 minutes to a reactor containing refluxing sulfuric acid (8.8 mL). Distillation occurred over a three hour period during which a total of 50 mL water was added to the refluxing mixture. HPLC indicated the reactor contained mostly 2,5-dichloroaniline and the distillate contained less than 1% 2,5-dichlorophenol generation.

Example 7

Diazotization in Acetic Acid/Sulfuric Acid

A. Diazotization Reaction 2,5-Dichloroaniline (8.95 mmol) was dissolved in acetic acid (16.9 mL, 32.9 equivalents) and sulfuric acid (5.4 mL, 11.2 equivalents) was then added. The 2,5-dichloroaniline initially remained in solution after addition of the sulfuric acid, but the solution became a thick, opaque, homogenous mixture as it was cooled to 10° C. Sodium nitrite was added drop wise as an aqueous solution (12.3 mmol, 1.4 equivalents, in 5.6 mL water). As sodium nitrite addition continued, 2,5-dichlorobenzene diazonium formed and was solvated. HPLC at this time indicated there was no remaining 2,5-dichloroaniline. The resulting 2,5-dichlorobenzene diazonium solution then was added drop wise to a refluxing (approximately 100° C.) solution of sulfuric acid (8.8 mL) and water (36 mL) in a reactor not equipped with a distillation arm, and stirred for 30 minutes. HPLC, however, did not indicate the presence of any 2,5-dichlorophenol in the refluxed solution. It is believed, however, that an increased reactor temperature and the addition of a distillation arm to the reactor would have resulted in the production of some amount of 2,5-dichlorophenol.

B. Diazotization Reaction (Sulfuric Acid Charge)

A study was conducted to evaluate the effect of the sulfuric acid charge on the conversion of 2,5-dichloroaniline to the diazonium. In this study, the acetic acid charge was maintained constant (18 equivalents) and the sulfuric acid charge was incrementally reduced.

Acetic acid (10.0 mL, 18 equivalents) was added to a series of beakers containing 2,5-dichloroaniline (1.50 g, 9.26 mmol). In separate experiments, decreasing equivalents of sulfuric acid (8.26 to 1.0 equivalents) were added to the beakers. The reaction mixtures were chilled in an ice bath (0° C. to 10° C.) and sodium nitrite$_{(aq)}$ (3.24 mL, 3 M, 1.05 equivalents) was added via syringe pump at a rate of 0.4 mL/minute with a subsurface flexible needle. After the addition was complete, the reaction mixtures were allowed to come to room temperature, and aliquots were removed for treatment with hypophosphorous acid to convert any diazonium produced to 1,4-dichlorobenzene. The relative ratios of the HPLC peak areas detected at 280 nm for the 2,5-dichloroaniline remaining and the 1,4-dichlorobenzene produced are reported in Table 7-A below and shown as a bar chart in FIG. 1.

TABLE 7-A

Diazonium Yield Versus Sulfuric Acid Charge

| SULFURIC ACID EQUIVALENTS | 2,5-DICHLOROANILINE (HPLC PEAK RATIO) | 1,4-DICHLOROBENZENE (HPLC PEAK RATIO) |
|---|---|---|
| 8.26 | 28.9% | 71.1% |
| 6.61 | 8.8% | 91.2% |
| 5.78 | 3.3% | 96.7% |
| 4.96 | 1.8% | 98.2% |
| 4.13 | 1.4% | 98.6% |
| 2.48 | 0.0% | 100.0% |
| 1.00 | 49.5% | 50.5% |

Reducing the sulfuric acid charge from 8.26 equivalents to 2.48 equivalents actually increased conversion of 2,5-dichloroaniline to the diazonium. Below 2.48 equivalents of sulfuric acid, however, conversion to the diazonium decreased.

C. Diazotization Reaction (Acetic Acid Charge)

A similar study also was conducted to evaluate the effect of the acetic acid charge on the conversion of 2,5-dichloroaniline to the diazonium. In this study, the sulfuric acid charge was maintained constant (2.5 equivalents) and the acetic acid charge was incrementally reduced.

Figure 2:
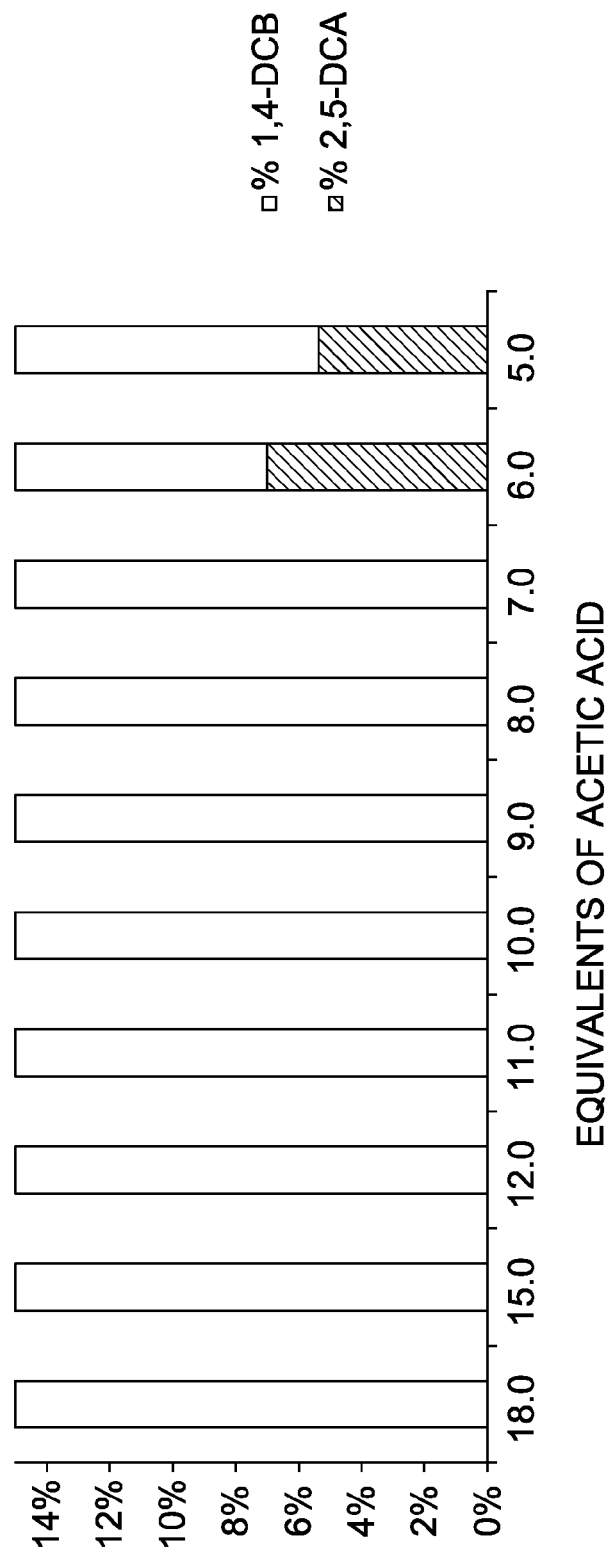
FIG. 2 is a bar chart illustrating the percent conversion (based on normalized peak absorbance at 208 nm by HPLC) of 2,5-dichloroaniline to 2,5-dichlorobenzenediazonium (quantified as 1,4-dichlorobenzene) as a function of equivalents of acetic acid relative to the 2,5-dichloroaniline.

Decreasing amounts of amounts of acetic acid (10 to 2.8 mL, 18 to 5 equivalents) were added to a series of beakers containing 2,5-dichloroaniline (1.50 g, 9.26 mmol). Sulfuric acid (2.27 mL, 2.5 equivalents) was then added to each beaker. The reaction mixtures were chilled in an ice bath (0° C. to 10° C.) and sodium nitrite(aq) (3.24 mL, 3 M, 1.05 equivalents) was added via syringe pump at a rate of 0.4 mL/minute with a subsurface flexible needle. After the addition was complete, the reaction mixtures were allowed to come to room temperature, and aliquots were removed for treatment with hypophosphorous acid to convert any diazonium produced to 1,4-dichlorobenzene. The relative ratios of the HPLC peak areas detected at 280 nm for the 2,5-dichloroaniline remaining and the 1,4-dichlorobenzene produced are reported in Table 7-B below and shown as a bar chart in FIG. 2.

TABLE 7-B

Diazonium Yield Versus Acetic Acid Charge

| ACETIC ACID EQUIVALENTS | 2,5-DICHLOROANILINE (HPLC PEAK RATIO) | 1,4-DICHLOROBENZENE (HPLC PEAK RATIO) |
| --- | --- | --- |
| 18.0 | 0.0% | 100.0% |
| 15.0 | 0.0% | 100.0% |
| 12.0 | 0.0% | 100.0% |
| 11.0 | 0.0% | 97.5% |
| 10.0 | 0.0% | 97.6% |
| 9.0 | 0.0% | 97.1% |
| 8.0 | 0.0% | 96.8% |
| 7.0 | 0.0% | 98.7% |
| 6.0 | 6.7% | 88.8% |
| 5.0 | 5.3% | 93.4% |

Reducing the acetic acid charge from 18.0 equivalents to 7.0 equivalents under the conditions tested did not materially decrease solubility or conversion to the diazonium. At acetic acid charges below 7.0 equivalents, however, decreases in solubility and conversion to the diazonium were observed.

D. Diazotization Reaction

A solution of acetic acid (7.78 mL, 7 equivalents) and sulfuric acid (4.54 mL, 2.5 equivalents) was added to a beaker containing 2,5-dichloroaniline (3.00 g, 18.52 mmol). The resulting mixture was chilled in an ice bath (0° C. to 10° C.) and sodium nitrite$_w$ (6.48 mL, 3 M, 1.05 equivalents) was added via syringe pump at a rate of 0.4 mL/minute with a subsurface flexible needle. After the addition was complete, the reaction mixture was allowed to come to room temperature, and an aliquot was removed for treatment with hypophosphorous acid to convert any diazonium produced to 1,4-dichlorobenzene. HPLC indicated complete conversion of the 2,5-dichloroaniline to 1,4-dichlorobenzene.

Example 8

Sodium Nitrite Equivalents

Figure 3:
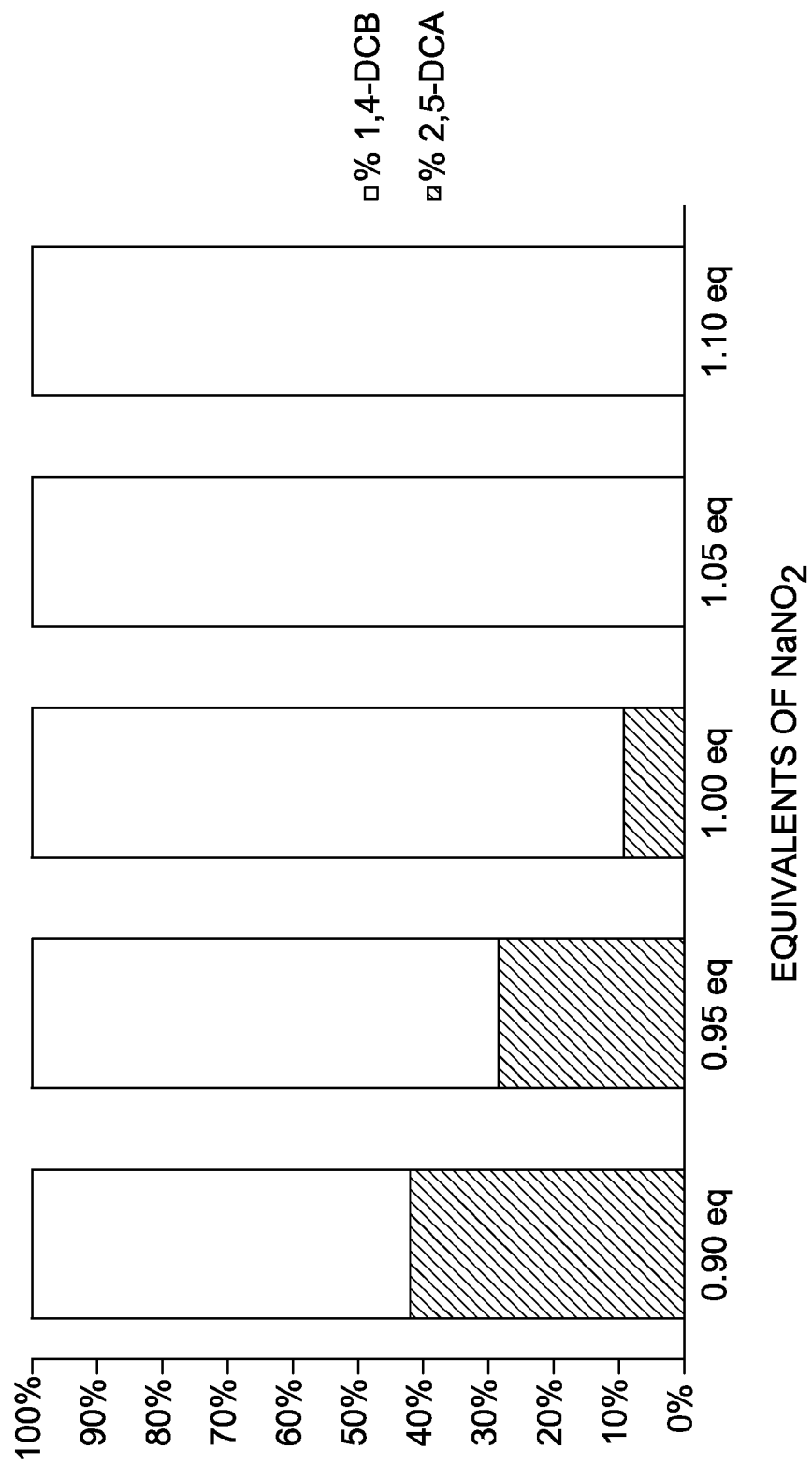
FIG. 3 is a bar chart illustrating the average percent conversion (based on normalized peak absorbance at 208 nm by HPLC) of 2,5-dichloroaniline to 2,5-dichlorobenzenediazonium (quantified as 1,4-dichlorobenzene) as a function of equivalents of sodium nitrite relative to the 2,5-dichloroaniline.

A study was conducted to evaluate the equivalents of sodium nitrate necessary for full conversion of 2,5-dichloroaniline to 2,5-dichlorobenzene diazonium. Specifically, five diazonium formation reactions were run with differing equivalents of sodium nitrite (0.90 to 1.10). In each case, 2,5-dichloroaniline (9.26 mmol) was dissolved in acetic acid (18 equivalents) and then sulfuric acid (8.26 equivalents) was added. The solution was chilled to 10° C. and sodium nitrite was added via syringe pump at a rate of 0.4 mL/min with a subsurface flexible needle. Each diazonium formation reaction was sampled at 30 minutes, 60 minutes, and 90 minutes, and the aliquot treated with 10× $H_3PO_2$ (50% by weight in water). The relative ratios of the HPLC peak areas detected at 280 nm for the 2,5-dichloroaniline remaining and the 1,4-dichlorobenzene produced are reported in Table 8-A and shown as a bar chart in FIG. 3. Each data point reported represents the average value for the three intervals measured because the formation of the 2,5-dichlorobenzene diazonium was very fast and there was no difference in the conversion over time. 2,5-Dichlorobenzene diazonium formation appeared to be complete between 1.00 and 1.05 equivalents of sodium nitrite.

TABLE 8-A

Diazonium Yield Versus Sodium Nitrite Charge

| | Equivalents Sodium Nitrite Relative to 2,5-Dichloroanaline | | | | |
| --- | --- | --- | --- | --- | --- |
| | 0.90 | 0.95 | 1.00 | 1.05 | 1.10 |
| Average % Peak Area: 2,5-Dichloroanaline | 42.0% | 28.4% | 9.3% | 0.0% | 0.0% |
| Average % Peak Area: 1,4-Dichlorobenzene | 58.0% | 71.6% | 90.7% | 100.0% | 100.0% |

2,5-Dichlorobenzene diazonium also was prepared at room temperature using the same acetic acid/sulfuric acid reaction medium described above and 1.05 equivalents of sodium nitrite. The mixture was stored at room temperature for two weeks and no degradation in the diazonium was observed.

Example 9

Sodium Nitrate Addition Method

A study was conducted to evaluate the effect of the method for adding sodium nitrite to the reaction medium containing the 2,5-dichloroaniline on the conversion of the 2,5-dichloroaniline to 2,5-dichlorobenzene diazonium.

In various experiments, sodium nitrite was added: (i) piecewise as a solid, (ii) as a solution in sulfuric acid, (iii) as an aqueous solution, or (iv) as pre-made nitrosylsulfuric acid. The primary objective was to evaluate whether such addition methods affected the in situ conversion of the nitrite to nitrous acid, the subsequent in situ conversion of the nitrous acid to nitrosylsulfuric acid, and/or the reaction of the nitrosylsulfuric acid with the 2,5-dichloroaniline to form the intended diazonium.

A. Addition of Solid Sodium Nitrite

Piecewise solid addition presented a challenge for consistent, controlled addition. When too much sodium nitrite was added to the sulfuric acid (i.e., all of the sodium nitrite did not dissolve immediately), the nitrous acid decomposed after formation. In general, when the solution temperature was too warm or the nitrite concentration was too high, the nitrous acid decomposed to water, nitrogen dioxide and nitric oxide. When decomposition occurred, gas evolution (an orange gas) and an increase in solution temperature were observed. When such decomposition occurred, a full equivalent of nitrous acid was not available to react with sulfuric acid to form nitrosylsulfuric acid in situ, and the reaction of such nitrosylsulfuric acid with the 2,5-dichloroaniline to form the intended amount of diazonium did not take place.

Sulfuric acid (20.23 g, 11.4 equivalents) was added to a beaker containing 2,5-dichloroaniline (3.00 g, 18.52 mmol). The reaction mixture was cooled to room temperature in an ambient water bath, and solid sodium nitrite (1.34 g, 19.44 mmol, 1.05 equivalents) was added piecewise over a period of 15 minutes. After the addition was complete, an aliquot was removed for treatment with hypophosphorous acid to convert any diazonium produced to 1,4-dichlorobenzene. HPLC indicated 94% conversion of the 2,5-dichloroaniline to 1,4-dichlorobenzene.

B. Addition of Sodium Nitrite in Concentrated Sulfuric Acid

An attempt was made to add a solution of sodium nitrite in concentrated sulfuric acid (greater than 4 M) to the solvent system containing the 2,5-dichloroaniline using a syringe pump. The addition was not successful because the pressure the pump applies to the syringe plunger caused the contents of the syringe to crystallize out of solution.

Sulfuric acid (30.07 g, 16.6 equivalents) was added to a beaker containing 2,5-dichloroaniline (3.00 g, 18.52 mmol). The reaction mixture was cooled to room temperature, and a solution of sodium nitrite (1.34 g, 1.05 equivalents) and sulfuric acid (8 g) was added drop wise via syringe with a subsurface needle. The syringe and needle became plugged when the sodium nitrite crashed out of solution under the pressure of the syringe. An additional 11.5 g of sulfuric acid was needed to solvate the syringe contents, and the resulting solution was added drop wise over a period of 30 minutes. After the addition was complete, the reaction mixture was allowed to come to room temperature, and an aliquot was removed for treatment with hypophosphorous acid to convert any diazonium produced to 1,4-dichlorobenzene. HPLC analysis indicated a 2,5-dichloroaniline to 1,4-dichlorobenzene peak absorbance ratio of 1:2.1.

C. Addition of Aqueous Solution of Sodium Nitrite

An aqueous solution of the sodium nitrite was added to a reaction medium containing the 2,5-dichloroaniline. When the aqueous solution was added to a reaction medium that was 2,5-dichloroaniline in concentrated sulfuric acid, the addition was very exothermic and analysis of the resulting solution showed a 2:1 ratio of diazonium to unreacted 2,5-dichloroaniline. In contrast, when the aqueous solution was added to a reaction medium that was 2,5-dichloroaniline in acetic acid/sulfuric acid, however, the reaction was mildly exothermic.

Sodium nitrite$_{(aq)}$ (2.2 M, 1.05 equivalents) was added drop wise to 2,5-dichloroaniline (18.52 mmol) in acetic acid/sulfuric acid and resulted in good conversion to the diazonium. Increasing the sodium nitrite concentration to 3 M also provided good conversion to the diazonium. When the sodium nitrite concentration was increased from 3 M to 6 M, however, conversion to the diazonium decreased to less than 70%. It is hypothesized that water plays a role in solvating the diazonium and sodium bisulfate (a byproduct of the formation of nitrous acid), and that sodium bisulfate precipitates out of solution as the amount of water present decreases.

Theoretically, the nitrous acid is less prone to decomposition and formation of the diazonium should be favored when the aniline sulfate solution is chilled to a temperature between 0° C. to 10° C. There did not appear to be a significant difference, however, in the formation of the diazonium at room temperature (about 25° C.) versus temperatures ranging from 0° C. to 10° C. The lower temperatures may not be required as long as stirring and subsurface addition of the sodium nitrite are adequate.

D. Addition of Nitrosylsulfuric Acid

Nitrosylsulfuric acid (40% by weight in concentrated sulfuric acid, Sigma-Aldrich) was added drop wise to a mixture of 2,5-dichloroaniline in sulfuric acid$_{(aq)}$ (60% by weight). The formation of the diazonium was quantitative, efficient, less exothermic, and less prone to decomposition. The reaction was repeated in 50% to 98% concentrated sulfuric acid with 2,5-dichloroaniline solubility increasing as sulfuric acid concentration increased. Similar results were obtained at all sulfuric acid concentrations, i.e., complete conversion to the diazonium.

To a beaker containing 2,5-dichloroaniline (3.00 g, 18.52 mmol) was added 60% by weight sulfuric acid$_{(aq)}$ (18.01 g, 110.17 mmol). The solution was warmed to 120° C. for 80 minutes to dissolve the 2,5-dichloroaniline. At room temperature, nitrosylsulfuric acid (40% by weight in sulfuric acid) (6.25 g, 1.06 equivalents) was added via pipette subsurface to the mixture. After the addition was complete, the reaction was allowed to come to room temperature, and an aliquot was removed for treatment with hypophosphorous acid to convert any diazonium produced to 1,4-dichlorobenzene. HPLC indicated 96% conversion of the 2,5-dichloroaniline to 1,4-dichlorobenzene.

As indicated by the experiments discussed above, the temperature and overall sodium nitrite concentration affect the mechanics of the sodium nitrite addition. One satisfactory approach (see Example 10) that resulted in complete conversion to the diazonium involved the addition of an aqueous solution of sodium nitrite (3 M) at a temperature of 10° C. via a subsurface flexible needle (16 gauge) as delivered by a syringe pump at 0.5 mL/min to the 2,5-dichloroaniline (18.52 mmol reaction scale) with overhead stirring in a mixed solvent system of acetic and sulfuric acid (7:2.5 molar ratio).

E. Drop Wise Addition to Concentrated Sulfuric Acid Reaction Medium 2,5-Dichloroaniline (18.52 mmol) was dissolved in concentrated sulfuric acid (8.27 mL, 8.38 equivalents) in a round-bottom flask equipped with an overhead stirrer. A solution of sodium nitrite (19.63 mmol, 1.06 equivalents) in sulfuric acid (8.27 mL, 8.38 equivalents) was added drop wise to a stirring mixture of 2,5-dichloroaniline sulfate salt at 10° C. HPLC analysis indicated that approximately 20% of the 2,5-dichloroaniline was unreacted. It is believed that due to solubility and handling conditions quantitative formation of the diazonium using only 1.05 equivalents of sodium nitrite is not likely in a concentrated sulfuric acid solvent system under these conditions. In addition, it is further believed that sodium nitrite in sulfuric acid (unlike sodium nitrite in an aqueous solution) is more likely to crash out of solution under increased pressure conditions (such as a syringe pump) at this concentration (0.164 g/mL). Using an addition funnel however, impedes delivery of the sodium nitrite which is better delivered subsurface and at a low steady rate (as it would have been using a syringe pump.

Example 10

Diazotization in Acetic Acid/Sulfuric Acid

A. Experiment A

Concentrated sulfuric acid (13.62 g, 0.14 mol, 2.50 equivalents) was added to a solution of 2,5-dichloroaniline (9.00 g, 0.055 mol) in acetic acid (23.35 g, 0.39 mol, 7.00 equivalents) in a 250 mL round-bottom flask. The addition of the sulfuric acid was exothermic. The reaction mixture was allowed to cool to room temperature. It remained solubilized and was stirred with an overhead paddle stirrer. The reaction mixture containing the 2,5-dichloroaniline was chilled (and became a slurry once cooled to 0° C. to 10° C.) and a solution of sodium nitrite (19.44 mL, 3 M, 1.05 equivalents) was added via syringe pump at 0.5 mL/minute. The flexible needle tip was placed subsurface of the solution and an ice water bath was used to maintain the solution at a temperature between 0° C. to 10° C.

Approximately 20 µL of the solution was removed and reacted with 100 µL of hypophosphorous acid (40% by weight in water) in a 2 dram vial. The aliquot was shaken for 30 seconds, diluted with 2 mL of methanol, and analyzed by HPLC to determine the ratio of unreacted 2,5-dichloroaniline to 1,4-dichlorobenzene (i.e., the product of the deamination reaction of diazonium with hypophosphorous acid). HPLC indicated approximately 100% conversion of the 2,5-dichloroaniline to the 1,4-dichlorobenzene.

B. Experiment B

Concentrated sulfuric acid (4.54 mL, 2.50 equivalents) was added to a solution of 2,5-dichloroaniline (3.00 g, 18.52 mmol) in acetic acid (7.78 mL, 7.00 equivalents) in a beaker. The reaction mixture was chilled in an ice bath (0° C. to 10° C.) and sodium nitrite (6.48 mL, 3 M, 1.05 equivalents) was added via syringe pump at a rate of 0.4 mL/minute with a subsurface flexible needle. After the addition was complete, the reaction mixture was allowed to come to room temperature, and an aliquot was removed for treatment with hypophosphorous acid to convert any diazonium produced to 1,4-dichlorobenzene. HPLC indicated approximately 100% conversion of the 2,5-dichloroaniline to 1,4-dichlorobenzene.

Example 11

Diazotization/Hydroxylation in Acetic Acid/Sulfuric Acid (Biphasic Reflux)

In three separate experiments similar to the experiments previously discussed in Example 3, sulfuric acid (15.00 g, 8.54 equivalents) was added to 2,5-dichloroaniline (8.95 mmol) in a solution of acetic acid (10.00 g, 18.61 equivalents). The mixture was stirred vigorously in a 100 mL beaker while the temperature was reduced to about 10° C. using a cold water bath. Sodium nitrite$_{(aq)}$ (1.21 or 1.37 equivalents as stated in Table 11-A) was added drop wise over 15 minutes to give a heterogeneous mixture. After the nitrite addition, sulfamic acid (0 equivalents to 0.11 equivalents) was added to the mixture and the mixture stirred for 10 minutes.

The mixture came to room temperature and was added via syringe pump to a reactor set at 130° C. and containing xylenes (40 mL) over a 15 minute to 90 minute period. The biphasic reaction mixture did not maintain the set temperature after the addition. The temperature stabilized at 97° C. to 111° C. even though the set temperature was at 130° C. The mixture was stirred for 30 minutes to 120 minutes. Stirring was stopped and the mixture was allowed to cool to room temperature, and the phases partitioned. The xylene layer was isolated and the 2,5-dichlorophenol yield determined using HPLC response factors. The 2,5-dichlorophenol product yields ranged from 1% to 34% as reported in Table 11-A below:

TABLE 11-A

| 2,5-Dichlorophenol Yield (Biphasic Reflux) | | | |
|---|---|---|---|
| Diazonium Solvent | Acetic/Sulfuric (4:3) | Acetic/Sulfuric (4:3) | Acetic/Sulfuric (4:3) |
| NaNO$_2$ Equivalents | 1.37 | 1.21 | 1.21 |
| NaNO$_2$ Addition | Aqueous | Aqueous | Aqueous |
| Nitrite Quench | None | None | Sulfamic |
| Reactor Temperature | 97° C. | 111° C. | 111 to 125° C. |
| % Unreacted DCA | 0% | 0% | 0% |
| % Yield 2,5-DCP | 33.41% | 1.78% | 8.40% |
| Clean Product Peak* | No | No | No |

*Refers to the HPLC of the organic phase post-hydrolysis.

The reported data indicate that the diazonium formation was complete, but that the conversion to the 2,5-dichlorophenol was very low under the biphasic conditions. As the 2,5-dichlorophenol formed, it was extracted into the xylenes. A phase partition of the reactor contents should have provided a 2,5-dichlorophenol product that could be distilled to produce clean 2,5-dichlorophenol. Analysis of the impurities in the organic phase with GCMS found nitrated xylenes and other byproducts present.

Example 12

Diazotization/Hydroxylation in Acetic Acid/Sulfuric Acid (Steam Distillation)

A. Hydrolysis with Water

Prior to employing the steam hydrolysis approach discussed below, an experiment was conducted to hydrolyze the diazonium in a reactor with water as described below.

Concentrated sulfuric acid (9.86 g, 11.23 equivalents) was added to a solution of 2,5-dichloroaniline (1.45 g, 8.95 mmol) in acetic acid (17.70 g, 32.94 equivalents) in a beaker. The reaction mixture was chilled in an ice bath (0° C. to 10° C.) and sodium nitrite (0.85 g, 1.37 equivalents) in water (6.50 mL) was added drop wise as to not raise the reaction temperature over 10° C. After the addition was complete, the reaction mixture was allowed to come to room temperature, and HPLC indicated no 2,5-dichloroaniline present. All of the aniline is presumed to have been converted to the diazonium.

To a three-neck round bottom flask equipped with a receiving flask was added water (20 mL) and sulfuric acid (10 mL). The solution was heated to 120° C., and the diazonium mixture (8.95 mmol) was added in portions over one hour. Water (2×20 mL) was added at one hour and two hours, and distillation continued for a total of four hours. The contents of the receiving flask were extracted with ethyl acetate to provide a 10% yield of 2,5-dichlorophenol while a 16% yield of 2,5-dichlorophenol was quantified in the reactor.

B. Hydrolysis with Water (Drop Wise Addition to Reactor)

An experiment was conducted to hydrolyze the diazonium with water added drop wise to the reactor via an addition funnel as described below.

Concentrated sulfuric acid (7.36 g, 8.38 equivalents) was added to 2,5-dichloroaniline (1.45 g, 8.95 mmol) in a beaker. The reaction mixture was chilled in an ice bath (0° C. to 10° C.) and sodium nitrite (0.81 g, 1.31 equivalents) in sulfuric acid (5 mL) was added drop wise as to not raise the reaction temperature over 10° C. After the addition was complete, the reaction mixture was allowed to come to room temperature.

To a three-neck round bottom flask equipped with a receiving flask containing 2,5-dichlorobenzenediazonium sulfate (8.95 mmol) was added water (25 mL) via an addition funnel over a two hour period while the reactor was heated to 120° C. The contents of the receiving flask were filtered by vacuum filtration to isolate solid 2,5-dichlorophenol (44% yield). The distillate filtrate was analyzed with response factors to give an additional 4.5% yield for 2,5-dichlorophenol.

C. Hydrolysis with Water (Present in Reactor)

Concentrated sulfuric acid (27.3 g, 24.1 equivalents) was added to a solution of 2,5-dichloroaniline (1.90 g, 11.74 mmol) in water (7.5 mL) in a beaker. The reaction mixture was chilled in an ice bath (0° C. to 10° C.) and sodium nitrite (0.97 g, 1.20 equivalents) in water (5 mL) was added drop wise over 10 minutes. After the addition was complete, the reaction mixture was allowed to come to room temperature. To a large vial containing 2,5-dichlorobenzenediazonium sulfate (11.7 mmol) was added water (20 mL), and the vial was heated to 100° C. for 2.5 hours. The reaction mixture was extracted with ethyl acetate and water, but no 2,5-dichlorophenol was detected.

D. Hydrolysis with Water (Steam Distillation—Effect of Temperature)

A study was conducted to evaluate the use of steam distillation at varying temperatures to hydrolyze the diazonium to the 2,5-dichlorophenol product.

Concentrated sulfuric acid (60.00 g, 8.26 equivalents) was added to a solution of 2,5-dichloroaniline (12.00 g, 0.074 mol) in acetic acid (80.00 g, 17.99 equivalents) in a beaker. The reaction mixture was chilled in an ice bath (0° C. to 10° C.) and sodium nitrite (5.37 g, 1.05 equivalents) in water (32 mL) was added subsurface via syringe pump as to not raise the reaction temperature over 20° C. After the addition was complete, the reaction mixture was allowed to come to room temperature, and HPLC indicated no 2,5-dichloroaniline present. All of the aniline is presumed to have been converted to the diazonium.

Sulfuric acid (40 mL) was added to a three-neck round bottom flask equipped with a side-arm condenser, receiving flask, and subsurface steam inlet, and heated to a set temperature for the trial (104° C., 130° C., or 150° C.). Steam was charged at a set rate of approximately 0.34 scf/minute. The diazonium mixture (19.6 mmol) was added via syringe pump at 0.8 to 1.25 mL/minute. At the end of the addition, the steam continued for 10 minutes then was turned off. The reactor was cooled to room temperature, and the yield of 2,5-dichlorophenol in the distillate and reactor were determined by response factors and summed. Results are reported in Table 12-A below. In general, 2,5-dichlorophenol yields were lower for reactions conducted at a temperature below 150° C.

TABLE 12-A 2,5-Dichlorophenol Yield Versus Reactor Temperature

| | | | |
|---|---|---|---|
| Reactor Set Temperature | 104° C. | 130° C. | 150° C. |
| Observed Exotherm | 160° C. | 185° C. | 195° C. |
| Unreacted Diazonium | 77.7% | 23.7% | 0.0% |
| % Yield 2,5-Dichlorophenol | 6.9% | 48.7% | 95.9% |

In addition, the amount of water in the distillate and the reactor was determined by Karl Fischer analysis. Any water added as part of a rinse or the diazonium solution was quantified and subtracted out to determine the amount of water added as steam. The amount of water collected and length of steam input into the reactor determine an approximate steam flow rate.

E. Hydrolysis with Water (Steam Distillation—Steam Rate)

A study was conducted to evaluate the use of steam distillation at varying steam rates to hydrolyze the diazonium to the 2,5-dichlorophenol product. Reducing the mass of water collected in the distillate can be beneficial for multiple reasons including situations where the 2,5-dichlorophenol product will be extracted with xylenes. The required amount of xylenes needed to extract 2,5-dichlorophenol was determined to be 85% by weight of xylene and 2,5-dichlorophenol solution (i.e., about 17 mL of xylenes for every 18.5 mmol of 2,5-dichlorophenol). Initial hydrolysis reactions employed about 0.3 scf/min to about 0.4 scf/min of steam and generated in excess of 300 g of water in the distillate. Additional hydrolysis reactions were conducted using reduced steam rates thereby lowering the mass of the distillate collected.

Sulfuric acid (40 mL) was added to a three-neck round bottom flask equipped with a side-arm condenser, receiving flask, and subsurface steam inlet, and heated to 150° C. Steam was charged at a set rate for each trial (0.38 scf/minute to 0.06 scf/minute). The diazonium mixture (18.52 mmol) was added via syringe pump at 1.25 mL/minute. At the end of the addition, the steam continued for five minutes then was turned off. The heat continued until the distillation head temperature dropped below 90° C. (approximately five minutes), then the reactor was cooled to room temperature. The yield of 2,5-dichlorophenol in the distillate and reactor were determined by response factors and summed. Results are reported in Table 12-B below.

TABLE 12-B 2,5-Dichlorophenol Yield Versus Steam Rate

| REACTION | ACID EQUIV. RATIO (ACETIC ACID:SULFURIC ACID) | YIELD SUM (%) | STEAM RATE (scf/min) | TOTAL MASS OF WATER COLLECTED (g) | LENGTH OF STEAM CHARGE (Minutes) |
|---|---|---|---|---|---|
| 1 | 18.0:8.3 | 91% | 0.35 | — | 40 |
| 2 | 18.0:2.5 | 84% | 0.38 | 312 | 39 |
| 3 | 7.0:2.5 | 95% | 0.18 | 117 | 31 |
| 4 | 7.0:2.5 | 96% | 0.10 | 57 | 24 |
| 5 | 7.0:2.5 | 89% | 0.06 | 31 | 23 |
| 6 | 7.0:2.5 | 84% | 0.09 | 42 | 22 |
| 7 | 7.0:2.5 | 81% | 0.10 | 42 | 23 |

Example 13

Hydrolysis in Acetic Acid/Sulfuric Acid (Steam Distillation)

A diazonium salt solution (prepared using an acetic acid/sulfuric acid medium) was loaded into a tared gas-tight syringe equipped with a 14 gauge flexible needle tip and weighed. Approximately 40 g of concentrated sulfuric acid (greater than 98% by weight) was added to a 250 mL 3-neck reactor equipped with a stir bar, side-arm condenser with receiving flask, sub-surface steam inlet, heating mantle, and JKEM temperature probe. When the acid temperature reached 150° C., steam was applied at approximately 0.1 scf/minute to 0.2 scf/minute. At the same time, addition of the diazonium solution began at 1.25 mL/minute with the tip of the flexible needle at near or sub-surface of the sulfuric acid. An initial exotherm gave a reactor temperature of 180° C. to 220° C. The distillation head maximum temperature reached 110° C.

At the end of the diazonium addition (approximately 10 minutes), the syringe was weighed to determine amount of diazonium added (18.51 mmol). The steam charge continued for 5 minutes post addition. The reactor was heated until the distillation head temperature lowered to 90° C. and no additional distillate was being collected (approximately 10 minutes). Some of the 2,5-dichlorophenol was a solid at the bottom of the receiving flask and some was dissolved in the distillate. The receiving flask contents were extracted with 17 mL xylenes (based on 15% by weight 2,5-dichlorophenol in the xylenes post-extraction) and the phases partitioned. 2,5-Dichlorophenol residue was present in the apparatus so the apparatus was rinsed with methanol and the washings were collected. HPLC quantitative analysis by response factors gave percent yield of 2,5-dichlorophenol in the distillate xylene phase (65.7%), distillate aqueous phase (5.1%), reactor residue (6.2%), and apparatus rinse (17.7%) were performed. Results of percent yield were summed to give an overall yield (94.8%). An aliquot from the reactor was treated with hypophosphorous acid to determine residual diazonium content (0%).

Proton NMR Data 2,5-dichlorophenol: $^1$H NMR (600 MHz, CDCl$_3$) δ 7.26 (d, 1H, J=10.2 Hz), 7.06 (d, 1H, J=2.4 Hz), 6.92 (dd, 1H, J=6.0, 2.4 Hz), 5.62 (br s, —OH).

2,5-dichloroaniline: $^1$H NMR (600 MHz, CD$_3$OD) δ 7.14 (d, 1H, J=8.4 Hz), 6.82 (d, 1H, J=2.4 Hz), 6.58 (dd, 1H, J=6.0, 2.4 Hz).

2,5-dichlorobenzenediazonium: $^1$H NMR (600 MHz, D$_2$O) δ 8.52 (d, 1H, J=2.4 Hz), 8.04 (dd, 1H, J=6.6, 2.4 Hz), 7.80 (d, 1H, J=9.0 Hz).

Example 14

Quench Prior to Hydrolysis Step

A study was conducted to evaluate the effect of quenching excess nitrous acid with sulfamic acid or urea necessary to prevent the formation of by-products in the hydrolysis step. Sulfamic acid and urea react with and decompose nitrous acid as shown below:

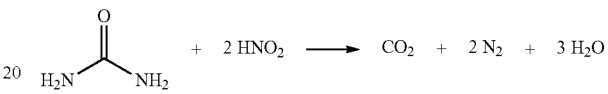

(1)

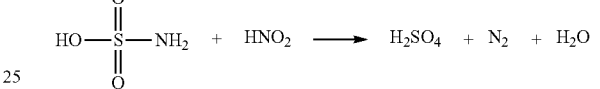

(2)

In this study, 2,5-dichlorophenol was stirred at 120° C. in the presence or absence of sodium nitrite and/or sulfamic acid. The 2,5-dichlorophenol itself was stable and either dissolved or melted in the various solvents at 120° C. Upon addition of sodium nitrite to the solution and heating at 120° C. for 30 minutes, all of the solutions had some byproduct formation. The experiments were repeated with sulfamic acid added at 1.1 times the sodium nitrite equivalents with heating to 120° C. for 30 minutes as before. Byproduct formation was reduced, and only the solutions containing sulfuric acid had byproducts. Results are reported in Table 14-A below.

TABLE 14-A 2,5-Dichlorophenol Stability at Specific Temperatures, Times, and Reagent/Solvent Conditions)

| CONDITIONS | WATER | WATER, XYLENES | SULFURIC ACID, WATER, XYLENES | ACETIC ACID, SULFURIC ACID, WATER |
|---|---|---|---|---|
| 60 minutes at 120° C. | No Byproducts | No Byproducts | No Byproducts | No Byproducts |
| 30 minutes at 120° C. 0.2 Eq. NaNO$_2$ | Possible Biphenyls | Nominal Byproducts | Nitrated DCP, Unidentified Byproducts, Possible Biphenyls | Nitrated DCP, Unidentified Byproducts, Possible Biphenyls |
| 30 min 120° C. 0.2 Eq. NaNO$_2$ 0.22 Eq. H$_3$SO$_3$N | No Byproducts | Nominal Byproducts | Unidentified Byproducts | Unidentified Byproducts |

Use of urea or sulfamic acid as described in this example did not appear to affect the yield of the 2,5-dichlorophenol in a hydrolysis reaction. A brown/orange reactor residue typically was observed in the hydrolysis reactions described in the prior examples. Use of urea or sulfamic acid, however, did not appear to reduce this reactor residue. In general, it appears that sulfamic acid or urea can be charged at 0.05% to 0.10% of the 2,5-dichloroaniline charge to offset the excess sodium nitrite charge, either as a solid or as an aqueous solution after the diazonium cools to room temperature.

Example 15

Parallel Addition of 2,5-Dichloroaniline and Nitroso Source

A. Parallel Addition of 2,5-Dichloroaniline and Nitrosylsulfuric Acid into Sulfuric Acid Solution Concentrated sulfuric acid (6.05 g, 0.06 mol, 0.5 eq.) was placed in a 250 mL three-neck round-bottom flask equipped with an overhead stirrer and cooled in an ice-water bath. A solution of 2,5-dichloroaniline in acetic acid (25 wt/wt %, 76.76 g, 0.12 mol) and a solution of nitrosylsulfuric acid in sulfuric acid (40 wt/wt %, 41.11 g, 1.08 eq.) were added in parallel via two individual syringe pumps. The addition of the aniline solution was carried out by dripping the solution into the stirring reaction while the addition of the nitrosylsulfuric acid solution was carried out by introducing the solution at the subsurface of the reaction medium. The addition rate was controlled such that both additions were completed in 41 minutes, during which time the reaction internal temperature was maintained below 15° C. After the addition, the formed diazonium salt solution was allowed to come to room temperature.

B. Parallel Addition of 2,5-Dichloroaniline and Nitrosylsulfuric Acid into a Mixed Solution of Acetic Acid and Sulfuric Acid Acetic acid (99%, 200.15 g, 3.33 mol, 5.4 eq.) was placed in a 1500 mL glass vessel equipped with an overhead stirrer. The solution was cooled in an ice-water bath and concentrated sulfuric acid (96%, 160.05 g, 1.57 mol, 2.54 eq.) was added. A solution of 2,5-dichloroaniline in acetic acid (26.0 wt/wt %, 384.6 g, 0.62 mol) and a solution of nitrosylsulfuric acid in sulfuric acid (40 wt/wt %, 202.5 g, 1.03 eq.) were added in parallel. The addition of the nitrosylsulfuric acid solution was carried out by introducing the solution at the subsurface of the reaction medium. The addition rate was controlled such that both additions were completed in 2.15 hours, during which time the reaction internal temperature was maintained between −4° C. to 10° C. After the addition, the formed diazonium salt solution was allowed to come to room temperature and was stirred at least for an additional 2 hours.

Experiment B was repeated except that a solution of 2,5-dichloroaniline in acetic acid (29.1 wt/wt %, 345.0 g, 0.62 mol) was used and the parallel additions were completed in 2.5 hours.

C. Parallel Addition of 2,5-Dichloroaniline and Sodium Nitrite into Sulfuric Acid Solution Concentrated sulfuric acid (15.84 g, 2.6 eq.) was placed in a 250 mL three-neck round-bottom flask equipped with an overhead stirrer and cooled in an ice-water bath. A solution of 2,5-dichloroaniline in acetic acid (19.23 wt/wt %, 50.91 g, 0.060 mol) was loaded into an addition funnel and a solution of sodium nitrite in water (20 wt/wt %, 22.30 g, 1.07 eq.) was loaded into a syringe pump. The addition of the sodium nitrite solution was carried out by introducing the solution at the subsurface of the reaction medium. The addition rate was controlled such that both additions were completed in 60 minutes, during which time the reaction internal temperature was maintained below 15° C. After the addition, the formed diazonium salt solution was allowed to come to room temperature.

D. Parallel Addition of 2,5-Dichloroaniline and Sodium Nitrite into a Mixed Solution of Acetic Acid and Sulfuric Acid Sulfuric acid (96%, 16.43 g, 2.50 eq.) and acetic acid (99%, 22.27 g, 5.70 eq.) were added to a 250 mL three-neck round-bottom flask equipped with an overhead stirrer. The flask was cooled in an ice-water bath. A solution of 2,5-dichloroaniline in acetic acid (24.8 wt/wt %, 42.07 g, 0.064 mol) was loaded into a tared gas-tight syringe and a solution of sodium nitrite in water (20 wt/wt %, 23.25 g, 1.04 eq.) was loaded into a separate syringe pump. The addition of the sodium nitrite solution was carried out by introducing the solution at the subsurface of the reaction medium. The addition rate was controlled such that both additions were completed in 90 minutes, during which time the reaction internal temperature was maintained below 15° C. After the addition was complete, the formed diazonium salt solution was allowed to come to room temperature.

E. Parallel Addition of 2,5-Dichloroaniline and Calcium Nitrite into a Mixed Solution of Acetic Acid and Sulfuric Acid In this experiment, calcium nitrite was used as the nitroso source in place of sodium nitrite. As with sodium nitrite, this alternate alkali metal likewise reacts with sulfuric acid to form nitrosylsulfuric acid in situ for diazotization of 2,5-dichloroaniline. Sulfuric acid (96%, 16.44 g, 2.5 eq.) and acetic acid (99%, 22.67 g, 5.78 eq.) were added to a 250 mL three-neck round-bottom flask equipped with an overhead stirrer. The flask was cooled in an ice-water bath. A solution of 2,5-dichloroaniline in acetic acid (25 wt/wt %, 42.73 g, 0.065 mol) was loaded into a tared gas-tight syringe, and a solution of calcium nitrite in water (10 wt/wt %, 45.28 g, 0.52 eq.) was loaded into a separate syringe pump. The addition of the calcium nitrite solution was carried out by introducing the solution at the subsurface of the reaction medium. The addition rate was controlled such that both additions were completed in 90 minutes, during which time the reaction internal temperature was maintained below 15° C. After the addition, the formed diazonium salt solution was allowed to come to room temperature. The insoluble solids were filtered and the filtrate was subjected for next hydroxylation step with water.

Diazonium salt solution filtrate (0.055 mol, 0.643 mmol/g) was loaded into a first tared gas-tight syringe equipped with a 14-gauge flexible needle tip. Water (50.86 g, 2.82 mol) was loaded into a second tared gas-tight syringe equipped with a 16-gauge flexible needle tip. Sulfuric acid (96%, 20 g) was placed in a 500 mL three-neck round-bottom flask equipped with a stir bar, a side-arm condenser with receiving flask, a heating mantle, and a JKEM thermocouple. When the acid temperature reached 150° C., the diazonium salt solution and water were added in parallel via aforementioned two syringe pumps. The addition rates were controlled such that the diazonium salt solution addition was completed in 72 minutes and the water addition was completed in 82 minutes. After 90 minutes, the heat was removed from the reactor and no additional distillate was collected afterwards. The contents in the receiving flask were weighed and isolated for analysis. HPLC quantitative analysis by response factors found the yield of 2,5-dichlorophenol in the distillate was 63.4%.

Example 16

Hydrolysis in Acetic Acid/Sulfuric Acid (Water)

A. Hydrolysis with Water (Parallel Addition of Water and Diazonium Solution)

Diazonium salt solution was prepared as in Example 15-A by parallel addition of 2,5-dichloroaniline and nitrosylsulfuric acid into a sulfuric acid solution. The diazonium salt solution (0.054 mol, 0.953 mmol/g) was loaded into a first tared gas-tight syringe equipped with a 14-gauge flexible needle tip. Water (46.0 g, 2.55 mol, 47.2 eq.) was loaded into a second tared gas-tight syringe equipped with a 16-gauge flexible needle tip. Sulfuric acid (85%, 20 g, 3.19 eq.) was placed in a 500 mL 3-neck round-bottom flask equipped with a stir bar, a side-arm condenser with receiving flask, a heating mantle, and a JKEM thermocouple. When the acid temperature reached 150° C., the diazonium salt solution and water were added in parallel via aforementioned two syringe pumps. The addition rates were controlled such that the diazonium salt solution addition was completed in 33 minutes and the water addition was completed in 70 minutes. The distillation head maximum temperature reached 110° C.

The reactor was heated when the distillation head temperature dropped below 90° C. and no additional distillate was collected at the end of approximately 85 minutes. The contents in the receiving flask were weighed and isolated for analysis. HPLC quantitative analysis by response factors found that the yield of 2,5-dichlorophenol in the distillate was 79.5%.

B. Hydrolysis with Water (Water Addition Before and after Parallel Addition of Water and Diazonium Solution)

Diazonium salt solution was prepared as in Example 15-B by parallel addition of 2,5-dichloroaniline and nitrosylsulfuric acid into a mixed solution of acetic acid and sulfuric acid. The resulting diazonium salt solution was evaluated for hydrolysis with water addition before and after the parallel addition of water and diazonium solution. The results show that the addition of water before and after the parallel addition improved the isolated 2,5-dichlorophenol yield.

Parallel Addition Only:

The diazonium salt solution was subjected to hydrolysis only by parallel addition of water and diazonium solution. Sulfuric acid (85% w/w, 502.7 g, 14.18 eq) was placed in a reaction vessel and heated to 150° C. Diazonium salt solution (0.62 mol, 0.683 mmol/g) and water (950 g, 52.75 mol) were added in parallel, during which the reaction internal temperature was maintained from 135° C. to 170° C. The addition rates were controlled such that both additions were completed in 5 hours 15 minutes. After 6 hours 35 minutes, the heat was removed from the reactor and no additional distillate was collected afterwards. The contents in the receiving flask were extracted into xylenes (3×300 g). HPLC quantitative analysis by response factors found that the yield of 2,5-dichlorophenol in the xylene extracts was 71.1%.

Water Addition Before and after Parallel Addition:

The diazonium salt solution was subjected to hydrolysis with water addition before and after the parallel addition of water and diazonium solution. Diazonium salt solution (0.49 mol, 0.652 mmol/g) was loaded into a first tared dropping funnel (500 mL). Water (880 g, 48.86 mol, 98.96 eq.) was loaded into a second tared dropping funnel (1000 mL). Sulfuric acid (85%, 432 g, 7.58 eq.) was added to a 1500 mL five-neck glass vessel equipped with a mechanical stirring, a side-arm condenser with receiving flask, and a heated oil bath. When the acid temperature reached 165° C., water (about 40 mL) was slowly added until a constant distillation of water in the distillation bridge was observed. At this time, the diazonium salt solution and water were added in parallel, during which the internal temperature maintained above 150° C. The addition rates were controlled such that the diazonium salt solution addition was completed in 7 hours as controlled by maintaining the internal temperature above 150° C. Additional water (approximately 40 mL) was added after the diazonium addition was completed and the heat source was then removed. The contents in the receiving flask were weighed and isolated for analysis. HPLC quantitative analysis by response factors found that the yield of 2,5-dichlorophenol in the distillate was 93.7%.

C. Hydrolysis with Parallel Addition (Water vs. Steam)

Diazonium salt solution was prepared as in Example 15-C by parallel addition of 2,5-dichloroaniline and sodium nitrite into sulfuric acid solution. The resulting diazonium salt solution was evaluated for hydrolysis by parallel addition of a hydrolysis source and the diazonium solution. The hydrolysis source was either water or steam.

Parallel Addition of Water:

The diazonium salt solution was subjected to hydrolysis by the parallel addition of water and diazonium solution. Diazonium salt solution (0.050 mol, 0.686 mmol/g) was loaded into a first tared gas-tight syringe equipped with a 14-gauge flexible needle tip. Water (55.79 g, 3.10 mol, 62.0 eq.) was loaded into a second tared gas-tight syringe equipped with a 16-gauge flexible needle tip. Sulfuric acid (77%, 20 g) was placed to a 250 mL three-neck round-bottom flask equipped with a stir bar, a side-arm condenser with receiving flask, a heating mantle, and a JKEM thermocouple. When the acid temperature reached 150° C., the diazonium salt solution and water were added in parallel via the two syringe pumps. The addition rates were controlled such that both additions were completed in 82 minutes. After 90 minutes, the heat was removed from the reactor and no additional distillate was collected afterwards. The contents in the receiving flask were weighed and isolated for analysis. HPLC quantitative analysis by response factors found that the yield of 2,5-dichlorophenol in the distillate was 55.6%.

Parallel Addition of Steam:

The diazonium salt solution was subjected to hydrolysis by the parallel addition of steam and diazonium solution. Diazonium salt solution (0.051 mol, 0.713 mmol/g) was loaded into a tared gas-tight syringe equipped with a 14-gauge flexible needle tip. Sulfuric acid (77%, 20 g) was placed in a 250 mL three-neck round-bottom flask equipped with a stir bar, a side-arm condenser with receiving flask, a heating mantle, and a JKEM thermocouple. When the acid temperature reached 150° C., the diazonium salt solution addition was started via the syringe pump and the steam charge (0.039 scf/min) was initiated. The addition rates were controlled such that the diazonium salt solution addition and the steam charge were completed in 90 minutes. After 90 minutes, the heat was removed from the reactor and no additional distillate was collected afterwards. The contents in the receiving flask were weighed and isolated for analysis. HPLC quantitative analysis by response factors found that the yield of 2,5-dichlorophenol in the distillate was 70.0%.

Example 17

Diazotization/Hydrolysis in Acetic Acid/Sulfuric Acid Containing Sodium Bisulfate A. Hydrolysis with Water (10% Spiked Sodium Bisulfate)

Diazonium salt solution was prepared as in Example 15-D by the parallel addition of 2,5-dichloroaniline and sodium nitrite into a mixed solution of acetic acid and sulfuric acid. The resulting diazonium salt solution was evaluated for hydrolysis with water in the presence of sodium bisulfate spiked in fresh sulfuric acid. The spiked sodium bisulfate was used to mimic the solvent system that would result from using recycled sulfuric acid in the process of diazotization and hydrolysis.

Diazonium salt solution (0.060 mol, 0.620 mmol/g) was loaded into a first tared gas-tight syringe equipped with a 14-gauge flexible needle tip. Water (57.00 g, 2.85 mol) was loaded into a second tared gas-tight syringe equipped with a 16-gauge flexible needle tip. Sulfuric acid (96%, 20 g) and sodium bisulfate (2.45 g, 0.34 eq.) were placed in a 500 mL three-neck round-bottom flask equipped with a stir bar, a side-arm condenser with receiving flask, a heating mantle, and a JKEM thermocouple. When the acid temperature reached 160° C., the diazonium salt solution and water were added in parallel via the two syringe pumps. The addition rates were controlled such that the diazonium salt solution addition was completed in 72 minutes and the water addition was completed in 82 minutes. After 90 minutes, the heat was removed from the reactor and no additional distillate was collected afterwards. The contents in the receiving flask were weighed and isolated for analysis. HPLC quantitative analysis by response factors found that the yield of 2,5-dichlorophenol in the distillate was generally around 88.0%.

B. Diazotization/Hydrolysis (10% Spiked Sodium Bisulfate)

Diazonium salt solution was prepared by parallel addition of 2,5-dichloroaniline and sodium nitrite into a mixed solution of acetic acid and sulfuric acid in the presence of spiked sodium bisulfate. The resulting diazonium salt solution was evaluated for hydrolysis with water in the presence of sodium bisulfate spiked in fresh sulfuric acid. The spiked sodium bisulfate was used to mimic the solvent system that would result from using recycled sulfuric acid in the process of diazotization and hydrolysis.

Sulfuric acid (96%, 16.43 g, 2.50 eq.), acetic acid (99%, 22.27 g, 5.70 eq.), and sodium bisulfate (0.81 g, 0.10 eq.) were added to a 250 mL three-neck round-bottom flask equipped with an overhead stirrer. The flask was cooled in an ice-water bath. A solution of 2,5-dichloroaniline in acetic acid (24.8 wt/wt %, 42.07 g, 0.064 mol) was loaded into a tared gas-tight syringe and a solution of sodium nitrite in water (20 wt/wt %, 23.25 g, 1.04 eq.) was loaded into a separate syringe pump. The addition rates were controlled such that both additions were completed in 90 minutes, during which the reaction internal temperature was maintained below 15° C. After the addition, the formed diazonium salt solution was allowed to come to room temperature.

Diazonium salt solution (0.059 mol, 0.615 mmol/g) was loaded into a first tared gas-tight syringe equipped with a 14-gauge flexible needle tip. Water (53.00 g, 2.65 mol) was loaded into a second tared gas-tight syringe equipped with a 16-gauge flexible needle tip. Sulfuric acid (96%, 20 g) and sodium bisulfate (2.45 g, 0.33 eq.) were placed in a 500 mL three-neck round-bottom flask equipped with a stir bar, a side-arm condenser with receiving flask, a heating mantle, and a JKEM thermocouple. When the acid temperature reached 160° C., the diazonium salt solution and water were added in parallel via the aforementioned two syringe pumps. The addition rates were controlled such that the diazonium salt solution addition was completed in 72 minutes and the water addition was completed in 82 minutes. After 90 minutes, the heat was removed from the reactor and no additional distillate was collected afterwards. The contents in the receiving flask were weighed and isolated for analysis. HPLC quantitative analysis by response factors found that the yield of 2,5-dichlorophenol in the distillate was 82.0%.

The experiments were repeated to show the consistent high yields of hydrolysis with water in the presence of sodium bisulfate spiked in fresh sulfuric acid. The results are shown in Table 17.

TABLE 17

Diazotization/Hydroxylation in Acetic Acid/Sulfuric Acid with Spiked Sodium Bisulfate

| Exp. No. | Diazotization $H_2SO_4$ source | Hydrolysis $H_2SO_4$ source/ spiked $NaHSO_4$ | DCP purity (area %) | DCP yield (%) |
|---|---|---|---|---|
| A-1 | fresh | fresh $H_2SO_4$/10.9% spiked $NaHSO_4$ | 98.3 | 88.2 |
| A-2 | fresh | fresh $H_2SO_4$/10.9% spiked $NaHSO_4$ | 98.5 | 87.5 |
| A-3 | fresh | fresh $H_2SO_4$/10.9% spiked $NaHSO_4$ | 99.0 | 88.1 |
| B | fresh/spiked $NaHSO_4$ | fresh $H_2SO_4$/10.9% spiked $NaHSO_4$ | 98.5 | 82.0 |

Example 18

Diazotization/Hydrolysis in Acetic Acid/Recycled Sulfuric Acid

A study was conducted to evaluate the feasibility of recycling the sulfuric acid used during the hydrolysis step and reusing that sulfuric acid in the diazotization/hydroxylation process steps. Results of the study indicate that the final product 2,5-dichlorophenol had consistent purities and yields when recycled sulfuric acid was used in the process. Such an approach for a commercial-scale process would be economically desirable.

A. Recycle of Sulfuric Acid from the Hydrolysis Reactor

After removing the heating mantle, the hydrolysis reactor was allowed to come to room temperature. The reactor was weighed and contents were poured or scraped into a 125 mL Erlenmeyer flask. The reactor was rinsed with a portion of xylenes and the xylene wash was added to the flask. The flask was heated to 100° C. and stirred for 15 minutes. The xylene was separated from the aqueous phase. The aqueous phase in the flask was treated with another portion of xylenes (100° C., 15 minutes) and the xylene was separated from the aqueous phase. The aqueous portion was cooled to room temperature for 1 hour. The sodium bisulfate salts that crashed out of solution were isolated by vacuum filtration on a sintered glass funnel. The solids were washed with a portion of xylenes. The salts were placed in a vacuum oven at 40° C. for 24 hours. After drying, the weight loss was measured and recorded. The filtrate was partitioned and the aqueous phase was isolated. The aqueous mixture was analyzed for water, sodium and sulfate content. The mixture had a composition of about 65% sulfuric acid, about 6% sodium bisulfate and about 29% water. The mixture was subjected to concentration or used directly for hydrolysis of diazonium salt in the next cycle.

B. Concentration of Recycled Sulfuric Acid

After the sulfuric acid was recycled from the hydrolysis reactor, as described in Example 18-A, the aqueous filtrate was subjected to concentration. The filtrate was transferred to a 100 mL three-neck round-bottom flask equipped with a stir bar, a side-arm condenser with receiving flask, a heating mantle, and a JKEM thermocouple. The contents in the reactor were gradually heated to 185° C., during which some distillation occurred. When the reactor temperature reached 185° C., vacuum was applied in a gentle mode first to prevent bumping and followed by slowly reducing the pressure to about 15 torr. The decreased temperature was observed during the active distillation. After no more distillation was observed at the reactor temperature of 185° C., both heating and vacuum were stopped. The concentrated sulfuric acid had a composition of about 90% sulfuric acid, about 2% water, and about 8% NaHSO4. The concentrated sulfuric acid was used in the next diazotization reaction.

C. Diazotization using Recycled and Concentrated Sulfuric Acid

Recycled and concentrated sulfuric acid (approximately 90%, 15.25 g, 0.14 mol, 2.16 eq.) and glacial acetic acid (99%, 22.99 g, 0.38 mol, 5.89 eq.) were added to a 250 mL three-neck round-bottom flask equipped with an overhead stirrer. The flask was cooled in an ice-water bath. A solution of 2,5-dichloroaniline in acetic acid (25 wt/wt %, 42.29 g, 0.065 mol) and a solution of sodium nitrite in water (20 wt/wt %, 23.84 g, 1.07 eq.) were added in parallel via two syringe pumps. The addition rates were controlled such that both additions were completed in 90 minutes, during which the reaction internal temperature was maintained below 15° C. After the addition, the formed diazonium salt solution was allowed to come to room temperature.

D. Hydrolysis using Recycled Sulfuric Acid

Diazonium salt solution (0.059 mol, 0.621 mmol/g) was loaded into a first tared gas-tight syringe equipped with a 14-gauge flexible needle tip. Water (50.22 g, 2.51 mol) was loaded into a second tared gas-tight syringe equipped with a 16-gauge flexible needle tip. Recycled sulfuric acid (about 65%, 29.66 g) was placed to a 500 mL three-neck round-bottom flask equipped with a stir bar, a side-arm condenser with receiving flask, a heating mantle, and a JKEM thermocouple. When the acid temperature reached 160° C., the diazonium salt solution and water were added in parallel via two syringe pumps. The addition rates were controlled such that the diazonium salt solution addition was completed in 60 minutes and the water addition was completed in 70 minutes. The distillation head maximum temperature reached 110° C. The reactor was heated when the distillation head temperature dropped below 90° C. and no additional distillate was collected at the end of approximately 80 minutes. The contents in the receiving flask were weighed and isolated for analysis. 2,5-Dichlorophenol residue was present in the distillation apparatus so the apparatus was rinsed with methanol. The washings were collected and quantified. HPLC quantitative analysis by response factors found that the yield of 2,5-dichlorophenol in the distillate was 88.5% and the yield of recovered 2,5-dichlorophenol from the apparatus rinse was 2.11%.

E. Diazotization/Hydrolysis Using Recycled Sulfuric Acid (Cycles)

The diazotization using recycled and concentrated sulfuric acid and hydrolysis using recycled sulfuric acid, as described in Examples 18-C and 18-D, were repeated for 7 cycles. Both purity and yield of 2,5-dichlorophenol in each cycle were evaluated. Results were presented in Table 18 and show both purities and yields were maintained for each cycle.

TABLE 18

Purity and Yield of 2,5-Dichlorophenol using Recycled Sulfuric Acid

| Cycle | Diazotization $H_2SO_4$ source | Hydrolysis Recycled $H_2SO_4$ source ($H_2SO_4$, $NaHSO_4$, $H_2O$) | DCP purity (area %) | DCP yield (%) |
|---|---|---|---|---|
| 1 | Recycle/concentrate | 57.95%, 7.51%, 34.54% | 97.3 | 86.4 |
| 2 | Recycle/concentrate | 57.95%, 7.51%, 34.54% | 98.3 | 84.6 |
| 3 | Recycle/concentrate | 57.95%, 7.51%, 34.54% | 98.9 | 83.1 |
| 4 | Recycle/concentrate | 61.13%, 9.12%, 29.75% | 96.4 | 86.3 |
| 5 | Recycle/concentrate | 61.13%, 9.12%, 29.75% | 96.6 | 85.9 |
| 6 | Recycle/concentrate | 61.13%, 9.12%, 29.75% | 98.9 | 90.6 |
| 7 | Recycle/concentrate | 61.13%, 9.12%, 29.75% | 97.4 | 84.3 |

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

What is claimed is:

1. A process for the preparation of a compound corresponding in structure to Formula (IV):

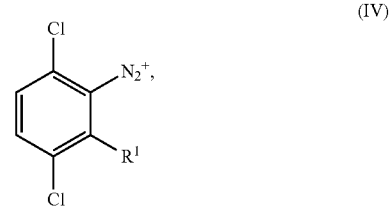

(IV)

or a salt thereof, the process comprising contacting a compound corresponding in structure to Formula (III):

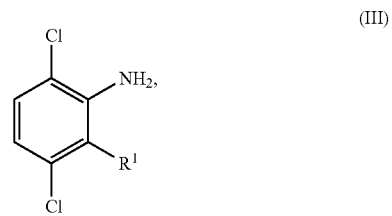

(III)

or a salt thereof, with a diazotizing agent in a reaction medium comprising sulfuric acid and an organic acid selected from the group consisting of $C_2$-$C_6$-alkanoic acids and halo-$C_1$-$C_6$-alkanoic acids to generate a diazonium product mixture comprising the compound or salt of Formula (IV);

wherein:

$R^1$ is selected from the group consisting of hydrogen, halogen, cyano, —$CH_3$, —$CH_2OH$, —$C(O)R^2$, —$C(O)OR^3$, and —$B(R^4)_2$;

$R^2$ is selected from the group consisting of hydrogen, $C_1$-$C_6$-alkyl, and —$NR^A R^B$; wherein $R^A$ and $R^B$ are independently selected from the group consisting of hydrogen and $C_1$-$C_6$-alkyl; and $R^3$ is selected from the group consisting of hydrogen and $C_1$-$C_6$-alkyl; and $R^4$ is selected from the group consisting of hydroxy and $C_1$-$C_6$-alkyl.

2. The process of claim 1, wherein $R^1$ is hydrogen.

3. The process of claim 1, wherein the organic acid is acetic acid.

4. The process of claim 1, wherein the diazotizing agent introduced into the reaction medium is nitrosylsulfuric acid.

5. The process of claim 1, wherein the diazotizing agent introduced into the reaction medium is an alkali metal nitrite selected from the group consisting of sodium nitrite and calcium nitrite.

6. The process of claim 1, wherein the process comprises concurrently introducing the diazotizing agent, the organic acid, and the compound or salt of Formula (III) into the reaction medium.

7. The process of claim 1, wherein the process comprises:
forming a reaction medium comprising sulfuric acid; the organic acid; and, optionally, a first amount of the compound or salt of Formula (III); and
introducing into the reaction medium a second amount of the compound or salt of the compound of Formula (III), and the diazotizing agent, to generate the diazonium product mixture comprising the compound or salt of Formula (IV).

8. The process of claim 1, wherein the process comprises:
forming a reaction medium comprising sulfuric acid; the organic acid; and the compound or salt of Formula (III); and
introducing into the reaction medium the diazotizing agent to generate the diazonium product mixture comprising the compound or salt of Formula (IV).

9. The process of claim 1, wherein the reaction medium comprises from about 1 molar equivalent to about 33 molar equivalents of the organic acid per mole of the compound or salt of Formula (III).

10. The process of claim 1, wherein the reaction medium comprises from about 1 molar equivalent to about 11 molar equivalents of the sulfuric acid per mole of the compound or salt of Formula (III).

11. The process of claim 1, wherein the molar ratio of the organic acid to the sulfuric acid is from about 30:1 to about 1:10.

12. The process of claim 1, wherein at least about 0.9 molar equivalent of the diazotizing agent per mole of the compound or salt of Formula (III) is introduced into the reaction medium.

13. The process of claim 1, wherein the process further comprises hydrolyzing the compound or salt of Formula (IV) to a compound corresponding in structure to Formula (V):

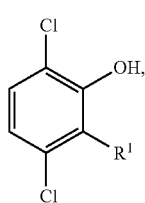

or a salt thereof.

14. The process of claim 13, wherein the hydrolysis step comprises concurrently adding the diazonium product mixture comprising the compound or salt of Formula (IV) and water to a reaction medium comprising sulfuric acid, and distilling to generate a phenol product mixture comprising the compound or salt of Formula (V).

15. The process of claim 13, wherein the hydrolyzing step comprises subjecting the diazonium product mixture comprising the compound or salt of Formula (IV) to steam distillation to generate the phenol product mixture comprising the compound or salt of Formula (V).

16. The process of claim 13, wherein the hydrolyzing step comprises:
combining the diazonium product mixture with an organic solvent to form a biphasic mixture comprising the compound or salt of Formula (IV); and
heating the biphasic mixture to generate the phenol product mixture comprising the compound or salt of Formula (V).

17. The process of claim 13, wherein the process further comprises recovering sulfuric acid and/or the organic acid from the hydrolysis step and recycling the recovered sulfuric acid and/or the organic acid to a prior process step.

18. The process of claim 1, wherein the process further comprises the step of reducing a compound corresponding in structure to Formula (II):

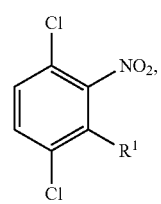

or a salt thereof, to generate the compound or salt of Formula (III).

19. The process of claim 13, wherein the process further comprises converting the compound or salt of Formula (V) to a compound of Formula (VI):

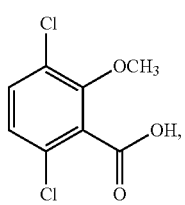

or a salt thereof.

20. The process of claim 13, wherein $R^1$ is hydrogen and the process further comprises:

carboxylating a compound or salt of Formula (V-a):

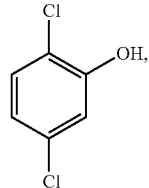

(V-a)

to generate a carboxylated product mixture comprising a compound corresponding in structure to Formula (V-b):

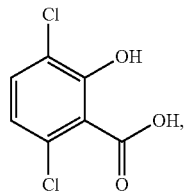

(V-b)

or a salt thereof;
methylating the compound or salt of Formula (V-b) to generate a methylated product mixture comprising a compound corresponding in structure to Formula (V-c):

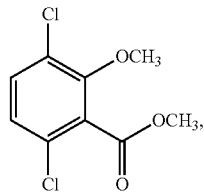

(V-c)

or a salt thereof; and
saponifying the compound or salt of Formula (V-c) to generate a dicamba product mixture comprising the compound or salt of Formula (VI):

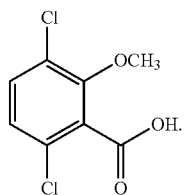

(VI)

* * * * *